United States Patent
Evke et al.

(10) Patent No.: US 12,152,910 B2
(45) Date of Patent: Nov. 26, 2024

(54) KIRIGAMI-BASED SENSOR DEVICES AND SYSTEMS

(71) Applicant: The Regents of the University of Michigan, Ann Arbor, MI (US)

(72) Inventors: Erin Evke, Ann Arbor, MI (US); Eugene Shteyn, Ann Arbor, MI (US); Max Shtein, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 720 days.

(21) Appl. No.: 17/294,172

(22) PCT Filed: Nov. 14, 2019

(86) PCT No.: PCT/US2019/061472
§ 371 (c)(1),
(2) Date: May 14, 2021

(87) PCT Pub. No.: WO2020/102527
PCT Pub. Date: May 22, 2020

(65) Prior Publication Data
US 2022/0003577 A1 Jan. 6, 2022

Related U.S. Application Data

(60) Provisional application No. 62/767,142, filed on Nov. 14, 2018.

(51) Int. Cl.
*G01L 1/22* (2006.01)
*G01D 11/30* (2006.01)
(52) U.S. Cl.
CPC ............... *G01D 11/30* (2013.01); *G01L 1/22* (2013.01)

(58) Field of Classification Search
CPC .. G01D 11/30; G01L 1/22; G01L 1/16; G01L 1/2287; A61B 5/1126; A61B 5/6804; A61B 2562/0261; A61B 2562/164
See application file for complete search history.

(56) References Cited

U.S. PATENT DOCUMENTS 8,191,433 B2   6/2012  Tao et al.
10,492,724 B2 * 12/2019  Beamer ................ A61B 5/6802
(Continued)

FOREIGN PATENT DOCUMENTS

JP   2015078967 A   4/2015
JP   2018105775 A   7/2018
(Continued)

OTHER PUBLICATIONS

D. H. Gates, L. S. Walters, J. Cowley, J. M. Wilken, L. Resnik, Range of Motion Requirements for Upper-Limb Activities of Daily Living; Am. J. Occup. Ther. 2016, vol. 70, 10 pp.
(Continued)

*Primary Examiner* — Suman K Nath
(74) *Attorney, Agent, or Firm* — Lempia Summerfield Katz LLC

(57) ABSTRACT

A sensor device includes a substrate having a plurality of cuts through the substrate to define a set of substrate sections, the substrate being flexible, and a plurality of sensor structures supported by the substrate, each sensor structure of the plurality of sensor structures being disposed at a respective substrate section of the set of substrate sections. Deformation of the substrate deforms each respective substrate section of the set of substrate sections such that each respective substrate section is deformed to a respective extent. Each sensor structure of the plurality of sensor structures is configured to provide an indication of the respective extent of the deformation.

35 Claims, 30 Drawing Sheets

(56) References Cited

U.S. PATENT DOCUMENTS

| | | | | |
|---|---|---|---|---|
| 11,013,463 | B2* | 5/2021 | Beamer | A61B 5/6802 |
| 2009/0282671 | A1 | 11/2009 | Tao et al. | |
| 2018/0303383 | A1* | 10/2018 | Connor | G06F 3/014 |

FOREIGN PATENT DOCUMENTS

| | | |
|---|---|---|
| KR | 20070106846 A | 11/2007 |
| KR | 20180116161 A | 10/2018 |
| WO | 2017179716 A1 | 10/2017 |
| WO | 2017218907 A1 | 12/2017 |

OTHER PUBLICATIONS

K. H. Mcveigh, P. M. Murray, M. G. Heckman, B. Rawal, J. J. Peterson, Accuracy and Validity of Goniometer and Visual Assessments of Angular Joint Positions of the Hand and Wrist; J. Hand Surg. 2016, vol. 41, e21-e35.

L. Xu, T. C. Shyu, N. A. Kotov; Origami and Kirigami Nanocomposites; ACS Nano 2017, vol. 11, 7587-7599.

S. Seyedin, J. Razal, P. C. Innis, A. Jeiranikhameneh, S. Beirne, G. G. Wallace; Knitted Strain Sensor Textiles of Highly Conductive All-Polymeric Fibers; ACS Appl. Mater. Interfaces 2015, vol. 7, 21150-21158.

Y. C. Chen, H. J. Lee, K. H. Lin, Measurement of body joint angles for physical therapy based on mean shift tracking using two low cost Kinect images; 2015 37th Annual Int. Conf. of the IEEE EMBC 2015, doi: 10.1109/ EMBC.2015.7318459; 703-706.

A. Glynn, H. Fiddler, The Physiotherapist's Pocket Guide to Exercise, Churchill Livingstone, Elsevier; 2009.

A. L. Lamoureux, Origami and Kirigami Design Principles for Optical Tracking, Energy Harvesting, and Other Applications, University of Michigan, 2017; 112 pp.

A. Rafsanjani, Y. Zhang, B. Liu, S. M. Rubinstein, K. Bertoldi; Kirigami skins make a simple soft actuator crawl; Sci. Rob. 2018, vol. 3, eaar7555; 8 pp.

Andrew Maimone et al.; Pinlight displays: wide field of view augmented reality eyeglasses using defocused point light sources; ACM Transactions on Graphics, vol. 33, No. 4, Article 89, 2014; 11 pp.

B. Gao, A. Elbaz, Z. He, Z. Xie, H. Xu, S. Liu, E. Su, H. Liu, Z. Gu; Bioinspired Kirigami Fish-Based Highly Stretched Wearable Biosensor for Human Biochemical-Physiological Hybrid Monitoring; Adv. Mater. Technol. 2018, vol. 3, 1700308; 8 pp.

B. Kim et al.; Mechanically Guided Post-Assembly of 3D Electronic Systems; Adv. Funct. Mater. 2018, vol. 28, 1803149; 11 pp.

E. M. Sluijs, G. J. Kok, J. van der Zee; Correlates of Exercise Compliance in Physical Therapy; Phys. Ther. 1993, vol. 73, 771-782.

F. Lorussi, N. Carbonaro, D. De Rossi, R. Paradiso, P. Veltink, A. Tognetti; Wearable Textile Platform for Assessing Stroke Patient Treatment in Daily Life Conditions; Front. Bioeng. Biotechnol. 2016, vol. 4, 16 pp.

G. Huang and Y. Mei, Assembly and Self-Assembly of Nanomembrane Materials—From 2D to 3D; Small 2018, vol. 14, No. 14, 23 pp.

H. Ko and A. Javey, Smart Actuators and Adhesives for Reconfigurable Matter, Accounts of Chemical Research, 2017; vol. 50, 691-702.

International Preliminary Report on Patentability cited in corresponding app. no. PCT/US2019/061472; May 18, 2021; 110 pp.

International Search Report and Written Opinion cited in corresponding application No. PCT/US2019/061472; Mar. 10, 2020; 15 pp.

J. Heikenfeld, A. Jajack, J. Rogers, P. Gutruf, L. Tian, T. Pan, R. Li, M. Khine, J. Kim, J. Wang, J. Kim; Wearable sensors: modalities, challenges, and prospects; Lab Chip 2018, vol. 18, 217-248.

Lee, J. H., Baker, L. L., Johnson, R. E., & Tilson, J. K.; Effectiveness of neuromuscular electrical stimulation for management of shoulder subluxation post-stroke: A systematic review with meta-analysis; Clinical Rehabil, 2017, vol. 31(11); 14 pp.

M. Blees et al.; Graphene kirigami; Nature 2015, vol. 524, 9 pp.

M. Gholami, A. Ejupi, A. Rezaei, A. Ferrone, C. Menon, Estimation of Knee Joint Angle Using a Fabric-Based Strain Sensor and Machine Learning: A Preliminary Investigation; Proc. 2018 IEEE Int. Conf. on Biomedical Robotics and Biomechatronics (BioRob) IEEE, 2018; 589-594.

M. Isobe, K. Okumura; Initial rigid response and softening transition of highly stretchable kirigami sheet materials; Sci. Rep. 2016, vol. 6, 6 pp.

Q. Wang, L. De Baets, A. Timmermans, W. Chen, L. Giacolini, T. Matheve, P. Markopoulos; Motor Control Training for the Shoulder with Smart Garments; Sensors 2017, vol. 17, 18 pp.

Q. Wang, P. Markopoulos, B. Yu, W. Chen, A. Timmermans; Interactive wearable systems for upper body rehabilitation: a systematic review, J. Neuroeng. Rehabil. 2017, vol. 14, 21 pp.

Q. Zhang, J. Wommer, C. O'Rourke, J. Teitelman, Y. Tang, J. Robison, G. Lin and J. Yin, Origami and kirigami inspired self-folding for programming three-dimensional shape shifting of polymer sheets with light; Extreme Mechanics Letters, 2017, vol. 11, 111-120.

R. C. Mather III, L. Koenig, D. Acevedo, T. M. Dall, P. Gallo, A. Romeo, J. Tongue, G. Williams Jr., The Societal and Economic Valueof Rotator Cuff Repair; J. Bone Joint Sur.; 2013, vol. 95, 1993-2000.

R. L. Gajdosik, R. W. Bohannon, Clinical Measurement of Range of Motion—Review of Goniometry Emphasizing Reliability and Validity; Phys. Ther. 1987, vol. 67, 1867-1872.

Radev, N.; Augmented Reality in Physiotherapy? [Video File]. Retrieved from https://youtu.be/OvCwvpJE6vo; Apr. 25, 2018.

S. K. Subramanian, C. L. Massie, M. P. Malcolm, M. F. Levin, Does Provision of Extrinsic Feedback Result in Improved Motor Learning in the Upper Limb Poststroke? A Systematic Review ofthe Evidence; Neurorehabilitation and Neural Repair 2010, vol. 24, 113-124.

S. M. Engdahl, D. H. Gates; Reliability of upper limb and trunk joint angles in healthy adults during activities of daily living; Gait Posture 2018, vol. 60, 41-47.

S. Ma, T. Ye, T. Zhang, Z. Wang, K. Li, M. Chen, J. Zhang, Z. Wang, S. Ramakrishna, L. Wei; Highly Oriented Electrospun P(VDF-TrFE) Fibers via Mechanical Stretching for Wearable Motion Sensing; Adv. Mater. Technol. 2018, vol. 3, 7 pp.

S. Sareh and J. Rossiter; Kirigami artificial muscles with complex biologically inspired morphologies, Smart Mater. Struct, vol. 22, 2013; 14 pp.

S. W. Castillo, N. Lezin, The Burden of Musculoskeletal Diseases in the United States: Prevalence, Societal and Economic Cost, 3rd ed., United States Bone and Joint Initiative, 2016; 12 pp.

T. C. Shyu et al.; A kirigami approach to engineering elasticity innanocomposites through patterned defects; Nat. Mater. 2015, vol. 14, 6 pp.

U. Gedalia, M. Solomonow, B. H. Zhou, R. V. Baratta, Y. Lu, M. Harris, Biomechanics of Increased Exposure to Lumbar InjuryCaused by Cyclic Loading; Spine 1999, vol. 24, 2461-2467.

X. Robert-Lachaine, H. Mecheri, C. Larue, A. Plamondon; Validation of inertial measurement units with an optoelectronic system for whole-body motion analysis; Med. Biol. Eng. Comput. 2017, vol. 55, 609-619.

Y. C. Liang, Applying kirigami models in teaching micro-electro-mechanical systems, 2013 3rd Interdisciplinary Engineering Design Education Conference, 2013, pp. 83-86, doi: 10.1109/IEDEC.2013.6526765.

Y. Menguc, Y.-L. Park, E. Martinez-Villalpando, P. Aubin, M. Zisook, L. Stirling, R. J. Wood, C. J. Walsh; Soft Wearable Motion Sensing Suit for Lower Limb Biomechanics Measurements; in Proc. 2013 IEEE International Conf. on Robotics and Automation, IEEE, 2013; 5309-5316.

Y. Yamamoto, S. Harada, D. Yamamoto, W. Honda, T. Arie, S. Akita, K. Takei; Printed multifunctional flexible device with an integrated motion sensor for health care monitoring; Sci. Adv. 2016, vol. 2, e1601473; 9 pp.

(56) References Cited

OTHER PUBLICATIONS

Y.-S. Guan, H. Li, F. Ren, S. Ren; Kirigami-Inspired Conducting PolymerThermoelectrics from Electrostatic Recognition Driven Assembly; ACS Nano 2018, vol. 12, 7967-7973.

Z. Wang, L. Zhang, S. Duan, H. Jiang, J. Shen and C. Li, Kirigami-patterned highly stretchable conductors from flexible carbon nanotubes-embedded polymer films, J. Mater. Chem. C, 2017, vol. 5, 11 pp.

Z. Yan et al.; Mechanical assembly of complex, 3D mesostructures from releasable multilayers of advanced materials, Sci. Adv. 2016, vol. 2, e1601014; 12 pp.

\* cited by examiner

KIRIGAMI-BASED SENSOR DEVICES AND SYSTEMS

CROSS-REFERENCE TO RELATED APPLICATION

This U.S. National Phase application is based on International Application No. PCT/US2019/061472, filed Nov. 14, 2019, which claims the benefit of U.S. provisional application entitled "Kirigami-Based Sensor Devices and Systems," filed Nov. 14, 2018, and assigned Ser. No. 62/767,142, the entire disclosures of which are hereby expressly incorporated by reference. Priority benefit of these earlier filed applications is hereby claimed.

STATEMENT REGARDING FEDERALLY SPONSORED RESEARCH OR DEVELOPMENT

This invention was made with government support under Contract No. EFMA1240264 awarded by the National Science Foundation. The government has certain rights in the invention.

BACKGROUND OF THE DISCLOSURE

Field of the Disclosure

The disclosure generally relates to wearables and other sensors.

Brief Description of Related Technology

Individuals often have improper positioning or movement during activities, such as lifting weights, and passive periods, e.g., sitting and sleeping with bad posture. Improper positioning or movement can lead to joint and muscular injuries. Recovery from injuries during physical therapy involves exercises to restore range of motion, however techniques and devices for detecting improper positioning are inadequate. For instance, goniometers are used to measure range of motion of a joint, but goniometers often poorly assess the complex motion presented by some joints (e.g., a shoulder joint), nor can be applied easily during the activity, especially if done dynamically and vigorously. Measuring the range of motion achieved during physical therapy, sports, and other exercises or tasks requires improvement. Without such measurements, it can also be difficult to track the extent to which a patient is performing a series of exercises prescribed by a physical therapist or a trainer. Individuals thus rarely uphold a prescribed regimen, leading to delays or failure to achieve desired results.

Recently, augmented reality (AR) and/or virtual reality (VR) techniques are being employed for the tracking in substantially real time the motion of a joint. Some AR/VR techniques depict, e.g., via a smartphone app, an extent to which a user is moving a limb, and whether a desired range of motion is achieved. However, current AR/VR approaches are problematic for a number of reasons. The smartphone apps lack integration with wearable sensors and are limited with respect to settings and sophistication of the tracking. More sophisticated and higher fidelity optical tracking has been achieved using multiple cameras in a studio environment. But such optical tracking typically involves expensive cameras with precise positioning needs, as well as separate optical tracking aids attached to joints.

Wearable sensors have been used to track or measure motion. For example, inertial measurement units (IMUs), which include an accelerometer, gyroscope, and magnetometer, generate various data to measure motion. Many of these units are packaged in the form of a rigid brace or integrated with a band, which are often uncomfortable and/or have limited functionality. For instance, in acute stroke patients, neuromuscular electrical stimulation with daily duration for about an hour reduces shoulder subluxation, or dislocation of the shoulder. Unfortunately, the use of IMUs alone cannot provide both positional tracking data and electrical stimulation, not to mention collect other useful data for thorough health monitoring, such as heart rate or temperature. In addition, there are several issues with braces currently used to provide structural support at the site of injury. For example, a brace placed on a patient to prevent re-injury or additional damage often leads to disuse atrophy or weakening of the muscles.

Conductive textiles have been used to collect positional data and improve the wearable aspect of sensing elements. In conductive textiles, the sensing elements are special fibers integrated into the textile. The sensing is based on stretching of the fibers, is typically unidirectional and poorly suited for integration with substantially rigid electronic components that do not tolerate mechanical deformation. In particular, interfaces between the textiles and electronic components are prone to failure.

SUMMARY OF THE DISCLOSURE

In accordance with one aspect of the disclosure, a sensor device includes a substrate having a plurality of cuts through the substrate to define a set of substrate sections, the substrate being flexible, and a plurality of sensor structures supported by the substrate, each sensor structure of the plurality of sensor structures being disposed at a respective substrate section of the set of substrate sections. Deformation of the substrate deforms each respective substrate section of the set of substrate sections such that each respective substrate section is deformed to a respective extent. Each sensor structure of the plurality of sensor structures is configured to provide an indication of the respective extent of the deformation.

In accordance with another aspect of the disclosure, a sensor system includes a processor, a memory in which tracking instructions and calibration data are stored, and a sensor module including a flexible substrate having a plurality of cuts through the substrate to define a kirigami structure, and a plurality of strain sensors supported by the flexible substrate, each strain sensor of the plurality of strain sensors being disposed at a respective location across the kirigami structure. Execution of the tracking instructions by the processor causes the processor to generate data indicative of displacement of the sensor module based on the calibration data and output signals from the plurality of strain sensors.

In connection with any one of the aforementioned aspects, the devices and methods described herein may alternatively or additionally include any combination of one or more of the following aspects or features. The plurality of cuts are arranged such that the set of substrate sections are disposed in a concentric arrangement. The concentric arrangement is symmetrical. The plurality of cuts are arranged such that the set of substrate sections are disposed in multiple concentric arrangements, the multiple concentric arrangements being connected with one another. The plurality of cuts are curvilinear. The plurality of cuts are straight. The substrate is capable of being disposed as a planar sheet. The plurality of sensor structures includes a flexible sensor structure. The set of substrate sections includes a respective beam along which the flexible sensor structure is disposed. The flexible sensor structure includes a strain sensor. The strain sensor includes a strain gauge. The sensor device or module further includes a rigid sensor structure, the rigid sensor structure being disposed adjacent to, and between, ends of a pair of the plurality of cuts. The rigid sensor structure includes an inertial measurement unit. The sensor device or module further includes a circuit in which the plurality of sensor structures are disposed, the circuit including a lead supported by the substrate and routed between adjacent cuts of the plurality of cuts. The circuit includes a power source supported by the substrate and disposed adjacent to ends of a pair of the plurality of cuts. The circuit includes a microcontroller supported by the substrate and disposed adjacent to ends of a pair of the plurality of cuts. The circuit includes an impulse generator supported by the substrate and disposed adjacent to ends of a pair of the plurality of cuts. The sensor device or module further includes a flexible adhesive layer that extends across a lateral extent of the substrate, the flexible adhesive layer being configured to adhere the sensor device to a subject. The plurality of sensor structures are disposed between the flexible adhesive layer and the substrate. The sensor device or module further includes a fabric layer worn by the subject. The flexible adhesive layer is disposed between the fabric layer and the plurality of sensor structures. The sensor device or module further includes a fabric layer worn by the subject. The fabric layer is disposed between the substrate and the subject. The flexible adhesive layer is configured as a patch to be adhered to an article of clothing or to equipment configured to protect the subject. The sensor module is a wearable module such that the displacement of the sensor module is representative of a three-dimensional curvature of a surface of the subject wearing the sensor module. The sensor system further includes a garment in which the sensor module is integrated. The sensor system further includes protective equipment configured to be worn by a user. The sensor module or device is integrated into the protective equipment. The protective equipment includes a joint brace. The sensor module or device includes an adhesive layer configured to adhere the sensor module to a subject. The displacement includes an angular displacement. The displacement includes a translational displacement. The execution of the tracking instructions causes the processor to determine a range of motion of a subject wearing the sensor module. The execution of the tracking instructions causes the processor to determine an activity type in which a subject wearing the sensor module is engaged via pattern analysis of the data indicative of the displacement. The sensor system further includes an impulse generator supported by the flexible substrate and configured to provide an impulse to a subject wearing the sensor module in response to a direction from the processor. The processor is configured to provide the direction based on an analysis of the data indicative of the displacement. The sensor system further includes a display in communication with the processor. The processor is configured to display images on the display in accordance with graphics instructions stored in the memory, the images being representative of the data indicative of the displacement. The sensor system further includes a microcontroller supported by the flexible substrate, the microcontroller including the processor and the memory. The memory includes a volatile memory unit in communication with the processor, and further includes a non-volatile storage device in which the calibration data is stored.

BRIEF DESCRIPTION OF THE DRAWING FIGURES

For a more complete understanding of the disclosure, reference should be made to the following detailed description and accompanying drawing figures, in which like reference numerals identify like elements in the figures.

Figure 26:
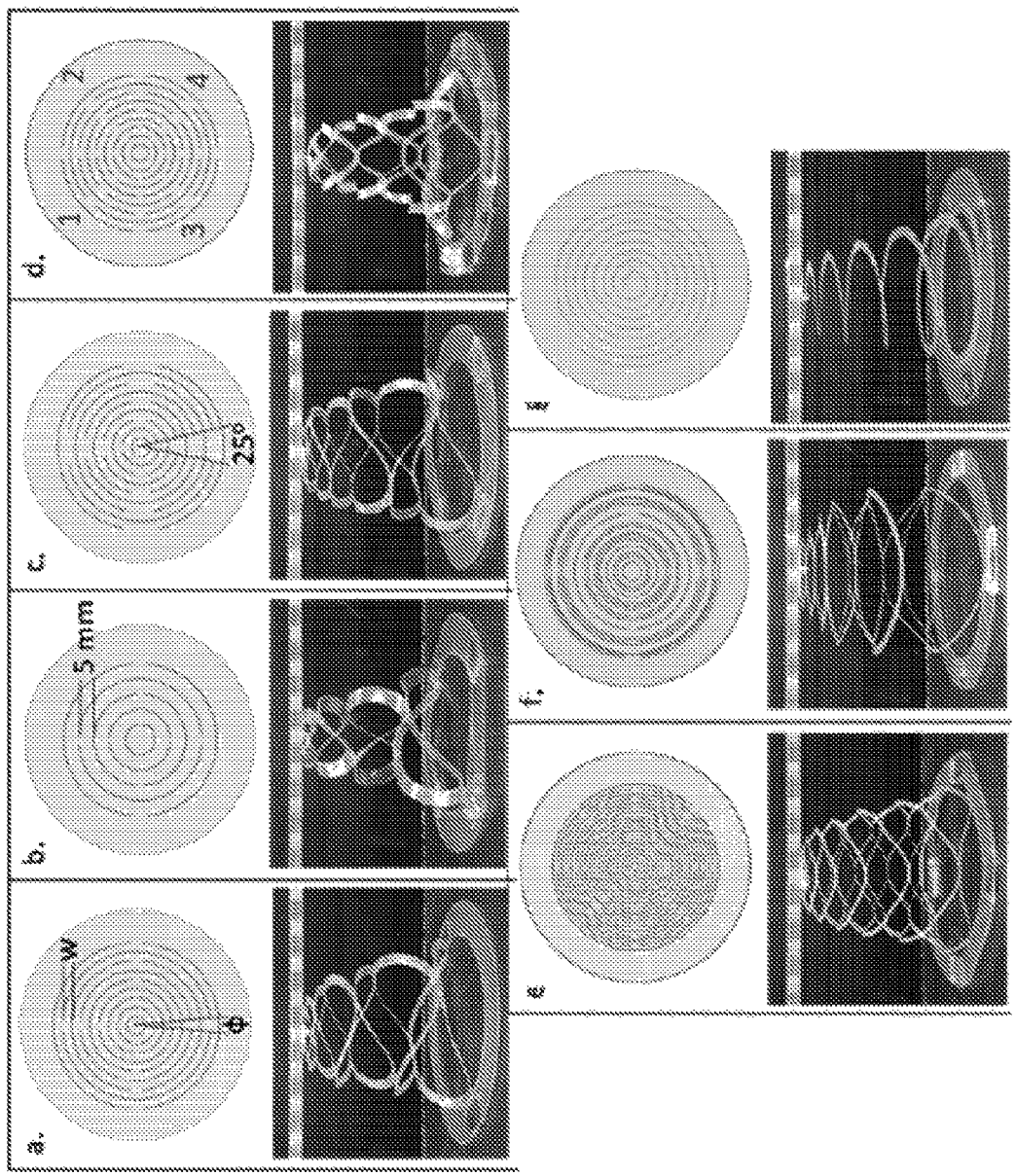

FIG. 26 depicts kirigami structures in accordance with a number of examples, before and after displacement, the examples having various cut patterns, radial spacing (w), angular spacing ($\phi$), and number of cuts along the perimeter ($N_{pc}$), including one example with unequal radial spacings. FIG. 26 also depicts another example having a single continuous cut to form a normal helical conical spring.

Figure 27:
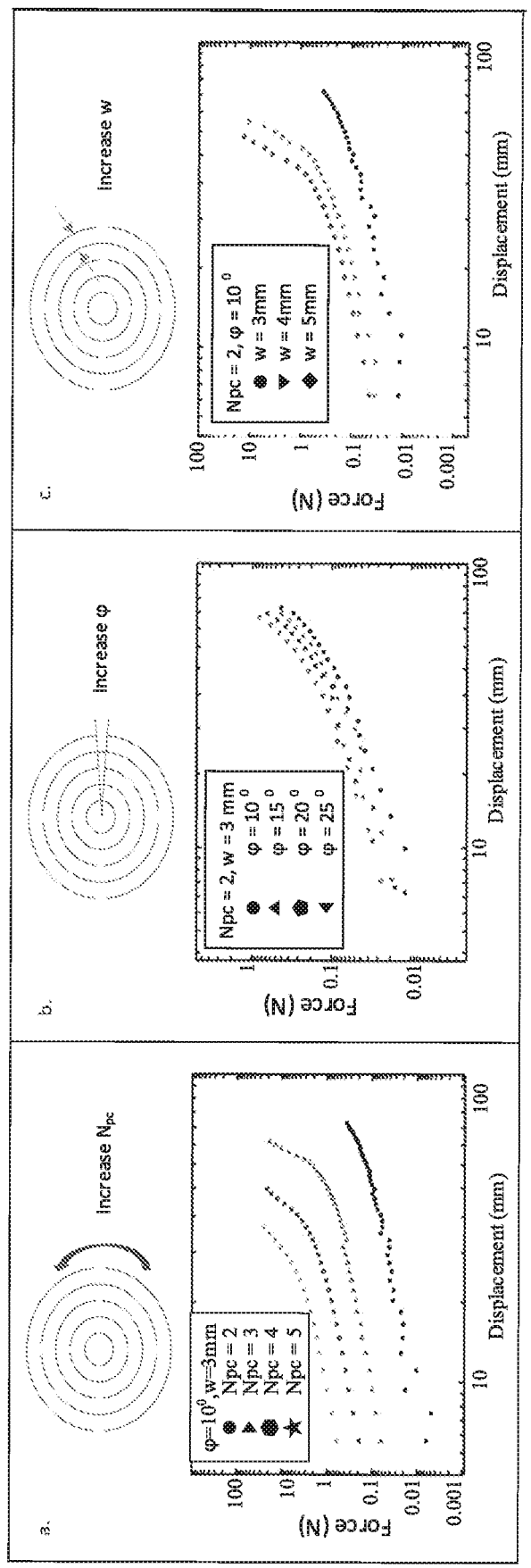

FIG. 27 depicts a number of plots showing logarithmic force versus displacement curves for a number of example cut patterns.

Figure 28:
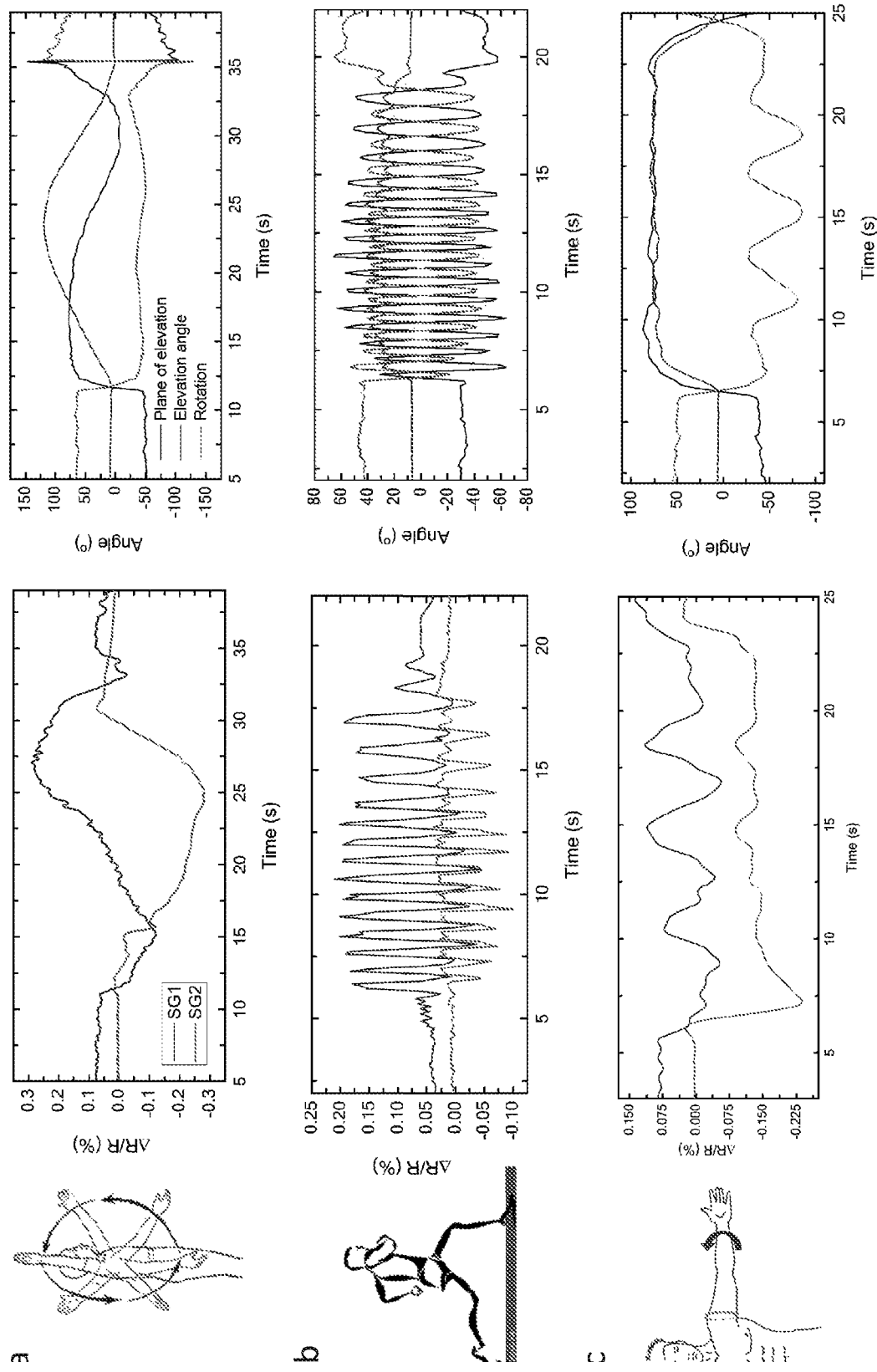

FIG. 28 depicts a number of plots showing resistance change and corresponding angular positions as various motions are performed.

Figure 29:
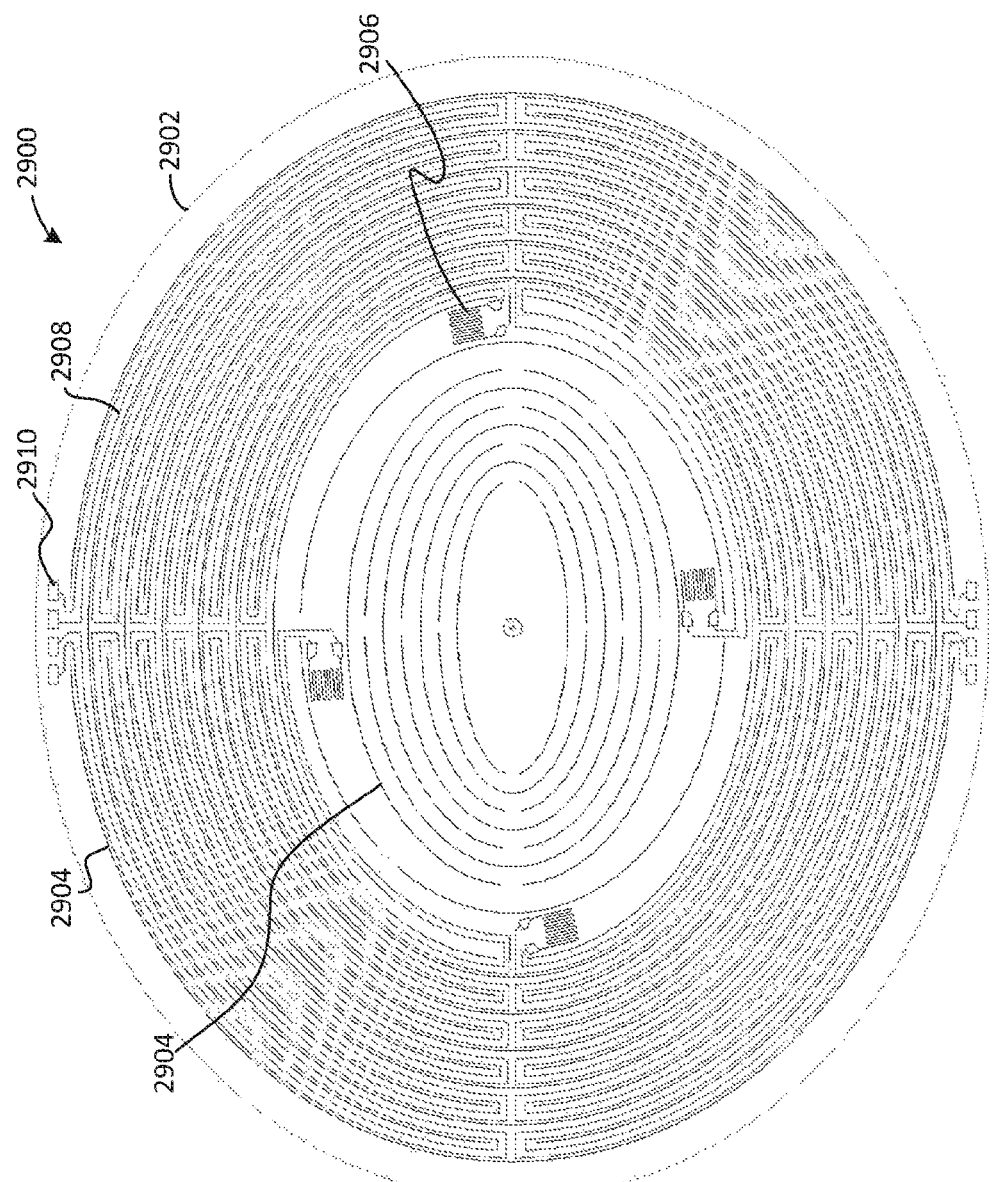

FIG. 29 is a schematic, plan view of a kirigami-based sensor device with integrated strain gauges in accordance with one example.

Figure 30:
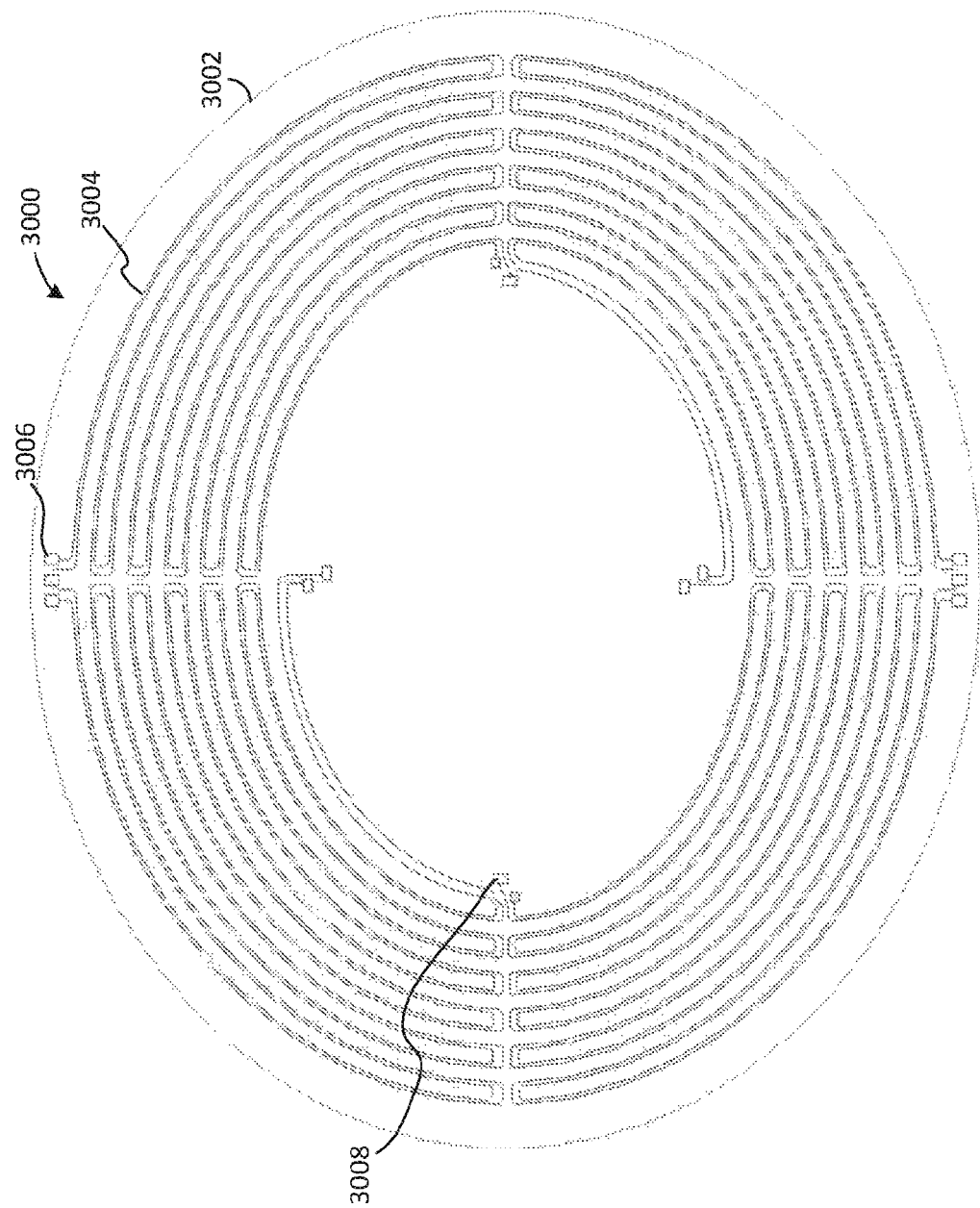

FIG. 30 is a schematic, plan view of a kirigami-based sensor device without strain gauges or substrate cuts to depict a circuit trace design in accordance with one example in greater detail.

While the disclosed sensor devices and systems are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF THE DISCLOSURE

Kirigami-based sensor devices and systems for providing data indicative of deformation and/or displacement are described. The sensor devices include a substrate with a plurality of cuts (e.g., straight or curvilinear cuts) to define a set of substrate sections, (here termed "beams"). The cuts are arranged in a kirigami pattern such that the substrate sections or beams deform into a series of alternating saddles. As a result, the substrate substantially conforms to a three-dimensional curvature or surface, such as a joint or other body part. The kirigami-like structures may or may not be symmetrical (e.g., rotationally symmetrical). Sensors, such as strain sensors, disposed on the substrate sections provide data or other indications of the extent of the deformation. The deformation may arise from the underlying surface (e.g., body), the movement of the body (e.g., subject), and/or the surrounding environment. In some cases, the sensor data is then used to determine a position or displacement.

The sensor devices and systems are useful in a number of different applications. Example applications or use scenarios include health monitoring, rehabilitation, training, and robotics. In each such case, the monitoring and data collected may be multi-dimensional in nature (e.g., three spatial dimensions and time). The sensor devices and systems may be used in conjunction or integrated with augmented reality or virtual reality systems. Other devices and systems, e.g. for training AI-based movement prediction algorithms, may also be integrated. The modular nature of the sensor devices allows the deformation data to be captured along with other data, such as temperature, heart rate, and/or other data. The deformation and other data may be stored in a network-connected data storage module or other data store of the disclosed systems. The contents of the data store may be analyzed using one or more protocols, according to the desired information, such as frequency, extent, and/or intensity of particular types of motion.

The disclosed devices and systems may be used to determine (e.g., approximate) a variety of different three-dimensional curvatures. The determinations may be static or dynamic. Examples of surfaces relevant to the disclosed devices and systems include but are not limited to various elements of the human body (e.g. muscles or joints of the shoulder, knee, wrist, hip, back, neck, etc.), elements of other animals, elements of mechanical systems, and elements of electromechanical systems. Although described below in connection with a number of examples involving joint motion, the disclosed devices and systems are also useful in various soft tissue contexts, including, for instance, monitoring muscle contraction (e.g., bicep flexing, weight distribution while sitting, standing, etc., posture while standing, etc.) and body morphological changes over time (e.g., slimming, etc.).

Figure 3:
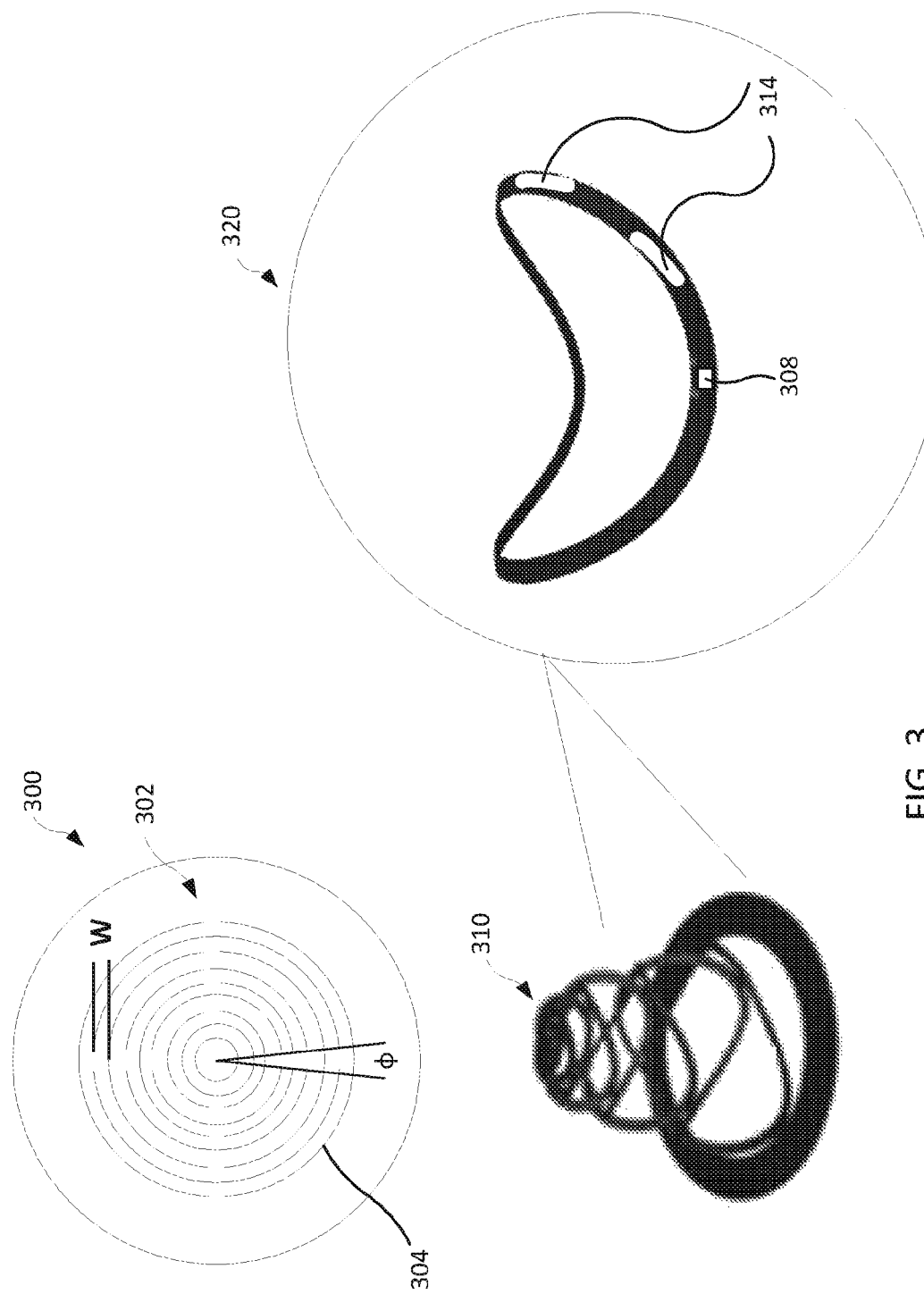
FIG. 3 are schematic plan and perspective views of a sensor substrate of a kirigami-based sensor device in accordance with one example.

The arrangement of cuts of the kirigami-based devices may be made to a substantially two-dimensional flexible substrate (e.g., a plastic sheet). The cuts may be straight or curved such that, when the structure is deflected (e.g., when the sheet is deformed perpendicular to its original plane), a saddle-like surface develops in the regions between the cuts (as illustrated in FIG. 3). The spaces between the cut ends experience substantially lower local stress and strain upon deflection compared to the spaces at the start of the cuts, as shown in, e.g., FIG. 3. Consequently, sensors placed in different locations are subject to different mechanical deformations. The difference in deformations leads to a distribution of points on the sheet, with some points experiencing negligible local strain, which increases the longevity and reliability of the sensors. This implementation is substantially improved from prior art on electronic textiles (e-textiles), where intrinsic stretchability of the substrate and/or sensor elements is commonly a limitation. Because the kirigami module of this invention originates as a flat (e.g., two dimensional) surface, the module may be more easily mass produced using robust and scalable processes. It is also modular, capable of being separately processed and embedded into common garments, sports accessories, patches, etc.

The stiffness of the kirigami module may be tuned or otherwise selected via a number of cut parameters, as well as the selection of substrate material and thickness. The disclosed sensor modules may thus be adaptable for a wide variety of objects, such as sleeves, bands, braces, therapeutic tapes, vests, leggings, and shorts. Additionally, the disclosed devices may be used to immobilize an injury, while permitting sufficient deformation to permit motion and prevent disuse atrophy.

Sensing and position location elements may be integrated on the same kirigami substrate, to which, the data from these sensing and/or positioning elements is correlated to procedures targeting athletic performance, rehabilitation, pharmaceutical procedures, games, ergonomics, etc. In some cases, the sensor data is processed in real time (e.g., effectively or substantially real time) to use in augmented/virtual reality and other applications.

Kirigami (i.e., the Japanese art of cutting) is used to engineer elasticity in the substrate. The cutting allows for greater control over the geometric design and device behavior. Various technologies (e.g. laser cutting, die cutting, printing, vapor coating, etc.) may be used to generate the two-dimensional patterns, with or without functional coatings, and thereby achieve device properties and performance in 2D-to-3D transformations via kirigami techniques. Curvilinear, piecewise linear, and other cut patterns may be used. The cut patterns may be useful in conforming to surfaces with complex curvature, which are useful robotic, human body (e.g., wearable), and other applications. The disclosed devices and modules approximate such curved surfaces, despite deforming from a planar sheet, which may be challenging using conventional flat sheets. To address this challenge, the planar kirigami sheets of the disclosed modules, may use repeating unit cells using fractal cuts, tessellations, cross minor, or other cuts. Lattice kirigami techniques may also be used to introduce dislocation and disclinations, which disrupt the lattice order in a material, causing out-of-plane deformation to relieve in-plain stress.

The kirigami-based nature of the disclosed devices and systems may used as a tool to geometrically manipulate the global structure and properties of materials. The kirigami modules may be discretized or otherwise considered as a series of beams. In this view, the segments between cuts act as hinges that cause the beams to bend out of plane with an applied stress. As a kirigami module is deformed, the beams defined by the cut lengths bend out of plane, creating a collection of saddle points with alternating positive and negative curvatures, enabling the structure to achieve large deflections. Upon cross-plane deformation, the kirigami module is capable of conforming to a globally curved surface with a shape that is accommodated by the cut geometry.

Figure 1:
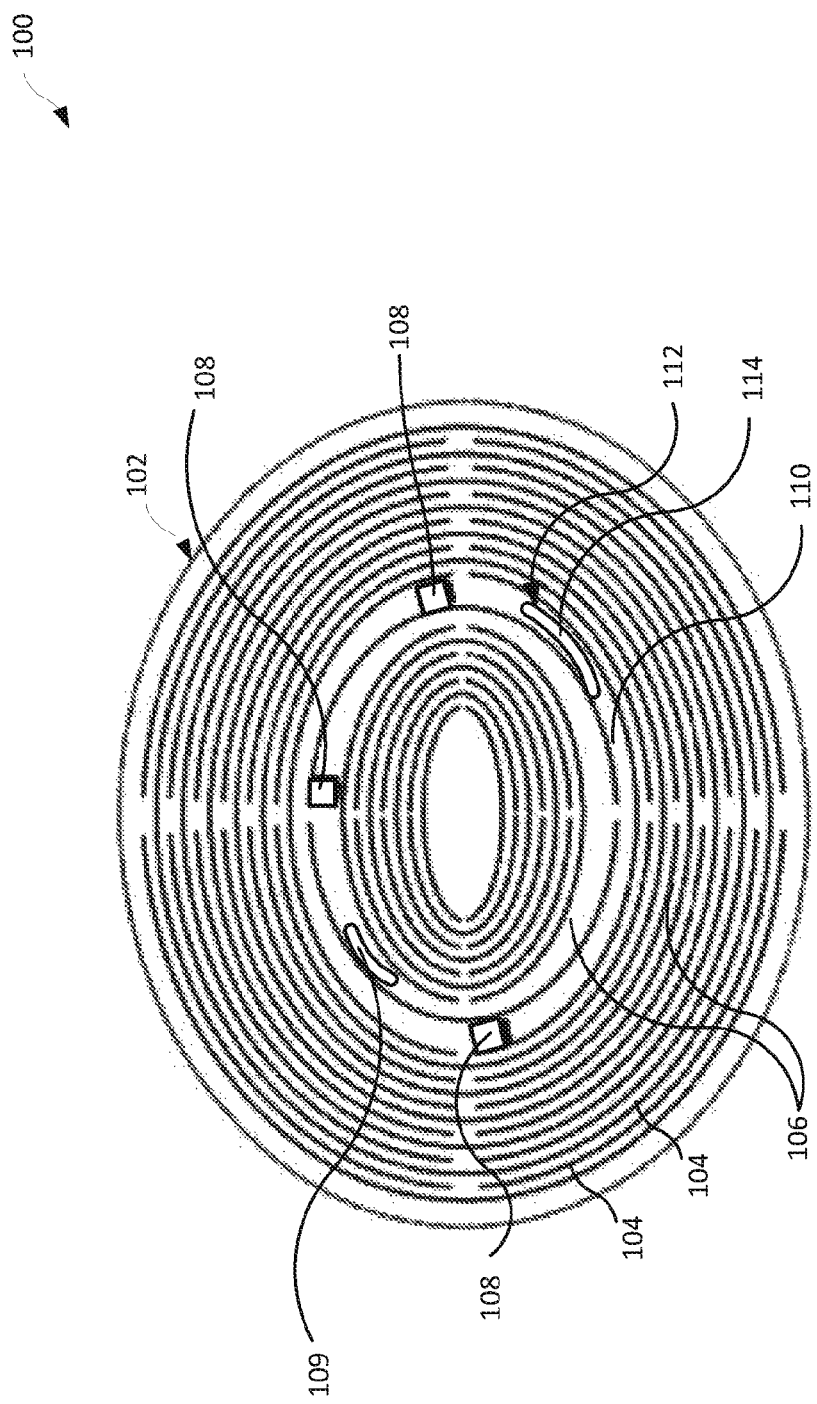
FIG. 1 is a schematic, plan view of a kirigami-based sensor device or module in accordance with one example.

FIG. 1 shows a sensor device 100 in accordance with one example. The sensor device 100 is configured for kirigami-based sensing of displacement or deformation of a three-dimensional surface. In some cases, the three-dimensional surface is a portion of the human body. The sensor device 100 may thus be wearable or other disposed in contact with or proximity to the body. Application areas include joints, such as the shoulders, elbows, and knees, as well as at muscle areas, such as the neck, triceps, and hip flexors. The sensor device 100 may be used in a variety of non-wearable applications, including, for instance, usage scenarios involving interactive surfaces (e.g., industrial controls and other user interfaces), machine interfaces (e.g., buttons), flexible tags (e.g. made of plastic electronics) other membranes or surfaces prone to failure.

The sensor device 100 includes a substrate 102. The substrate 102 may be a flexible substrate. The substrate 102 may be composed of, or otherwise include, a variety of materials including, for example, polymers, elastomers, shape memory polymers, shape memory alloys, foams, piezoelectric materials, thermoelectric materials, and silicon. The flexible nature of the substrate 102 enhances the ability to conform the sensor device 100 to various shapes. The substrate 102 may be used to support and connect different elements such as electronic components and sensors. The substrate material, thickness, shape, size, and other parameters may be selected to reduce or minimize the weight of the sensor device 100 and otherwise render the sensor device 100 more suitable for wearing and/or other deployment.

The substrate 102 may be a planar sheet prior to deformation. A planar sheet facilitates the integration of electronics, sensors and other elements supported by the substrate 102. Nonetheless, the substrate 102 may or may not be flat (e.g., effectively two-dimensional) prior to the deposition or disposition of sensing or other elements thereon.

A plurality of cuts 104 are made through the substrate 102 to define a set of substrate sections 106. Each section 106 may be configured as or considered to act like a deformable beam. Deformation of the substrate 102 deforms each respective substrate section 106 to a respective extent. As described herein, each respective extent of deformation is then captured to provide a three-dimensional mapping of the deformation (e.g., strain) of the substrate 102 and, accordingly, the surface to which the substrate 102 conforms.

The substrate 102 may be machined or otherwise processed to form the cuts 104 in a variety of ways. For example, laser- or etching-based processes may be used to cut the substrate 102.

The plurality of cuts 104 may be arranged such that the set of substrate sections are disposed in a substantially concentric arrangement. The concentric arrangement and the number of cuts may establish the kirigami-based deformation of the substrate 102.

The pattern of the cuts 104 may or may not be symmetric. In this case, the cuts 104 are curvilinear. In other cases, some or all of the cuts 104 are straight or otherwise not smooth. The shape of the cuts 104 may also vary from the circular pattern shown in FIG. 1. For instance, the cuts 104 may be arranged in an oblong shape, which may or may not match the shape or outline of the substrate 102. In some cases, the cut pattern and the substrate shape may match or otherwise be determined based on the shape and/or curvature of the body part. The geometry of the cuts 104 may thus differ significantly from the example shown.

The substrate sections 106 disposed between the cuts 104 act as hinges that cause the beams to bend out of plane with an applied stress. As the substrate 102 is deformed, the beams defined by the cuts 104 bend out of plane, creating a collection of saddle points with alternating positive and negative curvatures, enabling the substrate 102 to significantly deform. With such cross-plane deformation, the sensor device 100 is capable of conforming to a globally curved surface with a shape accommodated by the geometry of the cuts 104.

Figure 25:
FIG. 25 is a schematic, plan view of a kirigami-based sensor device having multiple connected kirigami structures configured for use as a shoe insert in accordance with one example.

The local and global flexibility of the sensor device 100 may be customized or otherwise configured for a given application. For example, the sensor device 100 may include one or more cut patterns for placement at regions of the foot. The sensor device 100 may thus be used as a shoe insert, or part of a sock or a sole of a shoe. Multiple cut patterns may be connected to one another of the sensor device 100 via a single substrate, forming one continuous sheet that conforms to the topology of the foot, an example of which is shown in FIG. 25.

The sensor device 100 includes a plurality of sensor structures 108 supported by the substrate 102. Each sensor structure 108 may be disposed at or along a respective substrate section 106. The sensor structures 108 include substantially flexible sensor structures configured to provide an indication of the respective extent of the deformation arising from the deformation. For example, the sensor structures 108 may be or include strain sensors (e.g., a strain gauge). Distribution of strain sensors across the substrate sections 106 may thus be used to provide a mapping of strain across the substrate 102. In some cases, the strain sensors are disposed at positions of maximum curvature, as defined by the cut pattern. The strain measurements provided by the strain sensors may be used, for instance, to determine position or other displacement of a body part. The displacement may be angular (rotational) or translational. For instance, the strain sensor measurements may be used to determine angular or rotational positions of a shoulder joint. Further examples of measurements and displacements supported by the sensor device 100 are described below.

The sensor structures 108 may be bonded or otherwise secured to the substrate 102. In some cases, the sensor structures 108 are bonded to the substrate 102 with an adhesive, such as epoxy resin. Alternatively or additionally, one or more of the sensor structures 108 are formed on the substrate 102 and thereby affixed thereto.

The strain sensors or other flexible sensor structure 108 may be disposed at various positions along one of the cuts 104. In the example of FIG. 1, two of the sensors 108 are disposed at the start of a respective cut 104. A maximum amount of deformation may occur at or near a cut start. The strain sensors at those locations may thus experience a high amount of strain. Other strain sensors may be disposed at other locations that experience lower amounts of strain. A mapping of the strain across the substrate 102 may thus be provided.

The number and locations of the sensors 108 may vary considerably from the example shown in FIG. 1. For instance, the total number of strain sensors may be significantly higher than those shown. A low number of strain sensors is depicted for ease in illustration. A higher number of strain sensors may be useful to provide a more complete mapping of strain across the substrate 102.

Other types of sensors may be supported by the substrate 102. The sensor structures may include rigid or other relatively non-flexible sensor structures. In the example of FIG. 1, the device 100 includes a non-flexible sensor structure 109 disposed along a beam 110. The rigid sensor structure 109 may be disposed on the substrate 102 in a location in which little deformation is present or possible. For example, the sensor structure 109 may be adjacent to, and between, the ends of a pair of the cuts 104.

The sensor structures 109 may be configured to detect, track, measure, or otherwise capture various physiological or non-physiological signals of the subject without being uncomfortable or invasive. Physiological examples include a heart rate, body temperature, blood pressure, respiration rate, arterial oxygen saturation, electrocardiogram (ECG), electromyogram (EMG), and electrodermal activity (EDA). Non-physiological examples include accelerometers, gyroscopes, and magnetic sensors. The non-flexible sensor structures 109 may be disposed at a position along the beam 110 that experiences minimal deformation. Such positioning may be useful to avoid or reduce stress on the sensor structures 109 as the substrate 102 deforms.

The substrate 102 may support a variety of different structures in addition to the sensors 108, 109. In the example of FIG. 1, the sensor device 100 includes an electronic unit 112. The electronics unit 112 is disposed along one of the substrate sections 106 (e.g., at a position that experiences a minimal or lower amount of deformation). The electronics unit 112 may include one or more electronic components. In this example, the electronics unit 112 is or includes an elongate circuit element 114 that extends along the substrate section 106. In some cases, the circuit element 114 acts as an antenna 114. Alternatively or additionally, the circuit element 114 is or includes a conductive line (e.g., a trace) that connects the electronics unit 112 to one or more of the sensor structures 108, 109. The positioning of the conductive line in a region of lower or minimal deformation may be useful for reducing, minimizing or preventing resistance changes outside of the sensor structures 108, 109, which would otherwise detrimentally affect the deformation or other measurements. Alternatively or additionally, the circuit element 114 may be configured such that deformation of the substrate 102 does not affect (e.g., significantly affect) the resistance. In other examples, the electronics unit 112 may be or include a microcontroller, which may be disposed in a central or other portion of the substrate 102 that provides sufficient space while experiencing minimal deformation.

The cut pattern may establish a wiring path for the components supported by the substrate. As described below, the wiring path may electrically connect a microcontroller with various components in addition to the strain sensors, including, for instance, accelerometers, gyroscopes, instrument amplifiers, an electrical impulse generator, and a power source (e.g., a battery).

Figure 2:
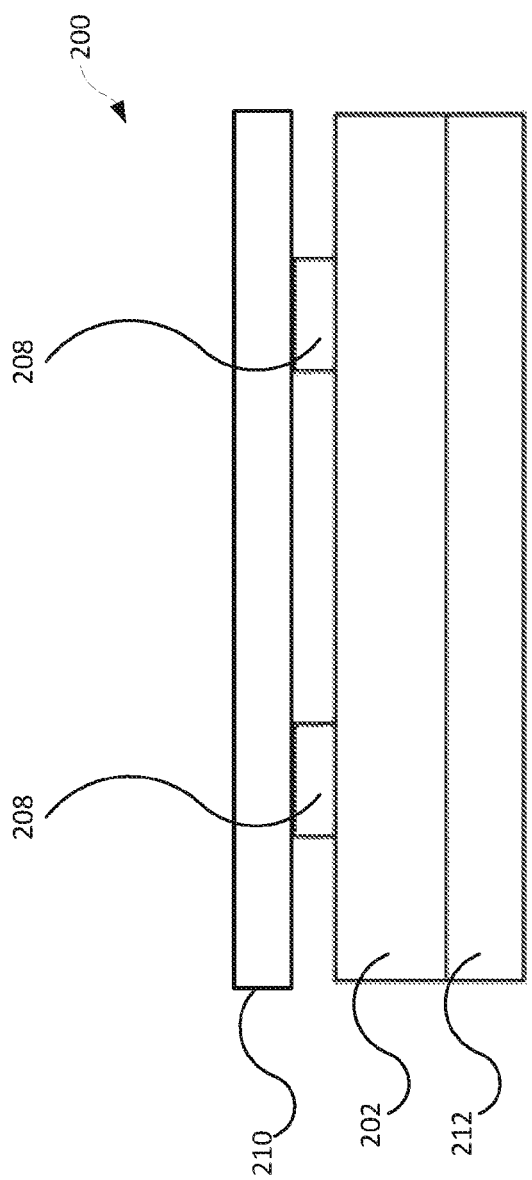
FIG. 2 is a schematic, side view of a kirigami-based sensor device or module in accordance with one example.

FIG. 2 shows a side view of a sensor device 200 in accordance with one example. The sensor device 200 includes a substrate 202 and a plurality of sensor structures 208. The sensor structures 208 may be or include strain sensors (e.g., strain gauges) and/or other sensors as described above. The substrate 202 and the sensor structures 208 may be disposed, arranged, and configured as described above. For instance, the substrate 202 has a cut pattern to allow for three-dimensional deformation of the substrate 202. The sensor device 200 may be configured similarly to the examples described above in other ways. For instance, the number, type, and other characteristics of the sensor structures 208 may vary as described above.

In the example of FIG. 2, the sensor device 200 includes a flexible adhesive layer 210 to adhere the sensor device 200 to a surface 212. The flexible adhesive layer 210 may or may not extend across the substrate 202 as shown. In other cases, the flexible adhesive layer 210 extends beyond, a lateral extent of the substrate 202. In some cases, the surface 212 is the surface of a garment or other item worn by a subject. The nature of the surface may vary. For example, the surface 212 is a skin surface of a subject in other cases involving an individual as the subject.

The flexible adhesive layer 210 is configured to allow the substrate 204 to conform to the surface of the subject 212. In one example, the flexible adhesive layer 210 is or includes Therapeutic Kinesiology tape (e.g., KT Tape®). The flexible adhesive layer 210 and the other layers or components of the sensor device 200 may be configured as a patch to be adhered to an article of clothing or equipment (e.g., a helmet or brace). A variety of sports and other tapes or layers may be used. In other cases, an insert into or of a garment may be used to position the sensor device 200 adjacent to a subject. For instance, the sensor device may be inserted into a pocket of a garment, and/or a compartment for a shoulder pad and/or a knee pad.

The sensor structures 208 are disposed on, or otherwise supported by, the substrate 202. In this example, the sensor structures 208 are disposed between the flexible adhesive layer 210 and the substrate 202. Other examples of sensor device arrangements are described below in connection with FIGS. 4-9.

FIG. 3 depicts a kirigami-based sensor device 300 both before and after deformation in accordance with one example. The sensor device 300 may correspond with one or more of the above-described examples, and/or be configured similarly thereto. The sensor device 300 accordingly includes a substrate 302 in which cuts 304 are made to define beams as described above. The sensor device 300 also includes a number of sensor structures 308, 314, such as strain sensors (e.g., strain gauges) and other types of sensors. Both flexible and rigid sensor structures may be included, as described above.

The substrate 302 of the sensor device 300 is shown as a planar sheet and in a deformed state 310. One of the beams is shown in greater detail in an exploded view 320. In this case, the sensor structure 308 is disposed along the beam in a region of minimal deformation, such as between the ends of two of the cuts 304. The sensor structure 308 may be rigid or otherwise more susceptible to failure upon deformation. In contrast, the sensor structures 314 are disposed along the beam in regions of increased deformation and, thus, may be configured to provide an indication of the extent of deformation. In such cases, the data captured by the sensor structures 314 may be used to measure the angular position of a joint, such as the shoulder joint.

Local and global stiffness of the sensor device 300, for a given selection of the substrate composition and thickness, is engineered through the geometry of the cuts 304. For instance, a greater number of cuts along the perimeter produces shorter beams 320 with an overall higher stiffness. Longer and more closely spaced (e.g. smaller w) produces lower stiffness. Using different dimensions and symmetries of the cut 104 patterns allows also to approximate complex surface curvatures better to fit different surfaces (e.g. a human foot). In some cases, the substrate 302 is or includes a polyethylene terephthalate (PET) sheet or film. The PET sheet may have a thickness of 90 micrometers, but other thicknesses may be used. The PET sheet may be laser-cut. The Young's modulus and Poisson's ratio of the film is 2.2

GPa and 0.37, respectively. In the example of FIG. 3, the cut kirigami sheet is deflected out of plane by, for instance, 50 mm.

FIG. 3 also depicts the manner in which the extent of deformation varies across the length of the beam. The hinge portion of the beam, where the beam is connected to another beam, has the ability to hold rigid sensors or components because little deformation occurs. The regions at the start of the cuts 304 experience the most bending, the greatest degree of curvature, and therefore support the flexible components, such as the strain sensors.

Several parameters of the cut pattern may be selected to customize the sensor device, including the radial spacing (w), angular spacing (φ), and number of cuts 104 along the perimeter ($N_{pc}$). In the example shown in FIG. 3, the radial spacing is 3 mm, the angular spacing is 10 degrees, and the number of cuts 104 along the perimeter is 2. The parameters may vary considerably. For instance, in other examples, the sensor device 100 may have unequal radial spacings, and/or may have a normal helical conical beam, having one continuous cut.

Each beam may be modeled as rings in series defined by its outer and inner radius ($R_o$ and $R_i$). The difference is the radial spacing. The applied concentrated force and pinned boundary conditions correspond to the uncut arc length designated by the cut pattern. The outer edges of the uncut regions of each ring are bounded by the previous ring, while the inner edges experience the load. Concentrated point loads are applied at the ends of each of the cuts 304, so for the baseline pattern that has two cuts along the circumference there are a total of four concentrated load points, assuming the forces are distributed equally. Therefore, the total force the beam 320 experiences is the sum of the concentrated point loads where the force versus displacement plot represents the concentrated force at one of the cuts, as seen. Assuming each ring experiences the same applied load, the total displacement of the beam is a sum of the individual displacements of each beam, where δ represents the displacement and R represents the outer radius. That is, $$\delta_{total} = \sum_{i}^{N_{rings}} \delta_{R_i}$$

The cut geometry may affect the displacement at which the material yields, as the displacement is influenced by the number of cut ends. Increasing the angular spacing increases the force to deflect the spring, and likewise, increasing the radial spacing increases the force to deflect the spring. This is due to the length of beams that are in bending. Regardless of the specific design changes whether $N_{pc}$, φ, and/or w, when the beams are shortened, the force to achieve the same displacement is increased. While the regimes are typically designated as approximately linear for small deformations or nonlinear for larger deformations, there is a transition regime, as well as a regime where plastic deformation becomes more significant.

In one implementation, the resistance of the strain gauge(s) changes upon elongation. The resistance change is computed to determine the strain, which corresponds to the angular position of the joint, enabling user moving the joint being detected. In some cases, rosette strain gauges are used in which three strain gauges are stacked 0°, 45°, and 90°. The rosette strain gauge is connected to a Wheatstone Bridge in a quarter bridge configuration to detect very small changes in the resistance, within milli-Ohms. The following are equations to determine the principal strain from the strain given from each strain gauge where E represents strain.

$$\epsilon_0 = \frac{\epsilon_x + \epsilon_y}{2} + \frac{\epsilon_x - \epsilon_y}{2}$$

$$\epsilon_{45} = \frac{\epsilon_x + \epsilon_y}{2} + \frac{\gamma_{xy}}{2}$$

$$\epsilon_{90} = \frac{\epsilon_x + \epsilon_y}{2} - \frac{\epsilon_x - \epsilon_y}{2}$$

Therefore, $\epsilon_x = \epsilon_0$, $\epsilon_y = \epsilon_{90}$, and $\gamma_{xy} = 2\epsilon_{45} - (\epsilon_0 + \epsilon_{90})$.

FIGS. 4-9 are schematic, side views of further kirigami-based sensor devices in accordance with several examples. The examples present several substrate-sensor arrangement and integration options.

Figure 4:
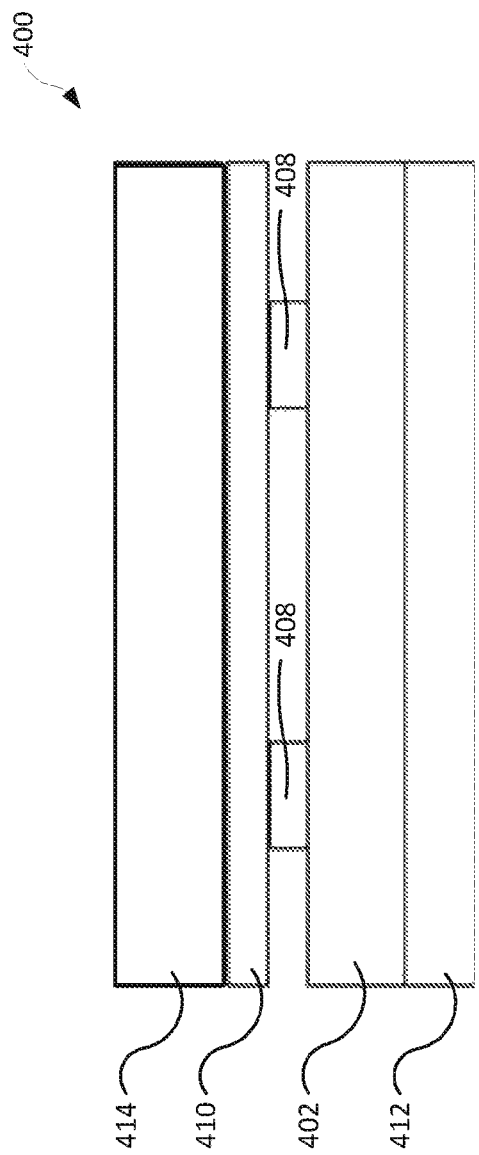
FIGS. 4-9 are schematic, side views of further kirigami-based sensor devices in accordance with several examples.

FIG. 4 depicts a side view of a sensor device 400 integrated with a fabric layer according to one example. In this example, the sensor device 400 includes a substrate 402 and a plurality of sensor structures 408. The sensor structures 408 are supported by the substrate 402. The sensor device 400 further includes a flexible adhesive layer 410 and a fabric layer 414. In some cases, the fabric layer 414 constitutes part of an article of clothing worn by a subject 412. Other fabric integration options are possible, including for instance, a patch as described above. The flexible adhesive layer 410 is disposed between the fabric layer 414 and the sensor structures 408. The flexible adhesive layer may extend across a lateral extent of the substrate 402. The flexible adhesive layer 410 is configured to adhere the sensor structures 408 to the subject 412.

Figure 5:
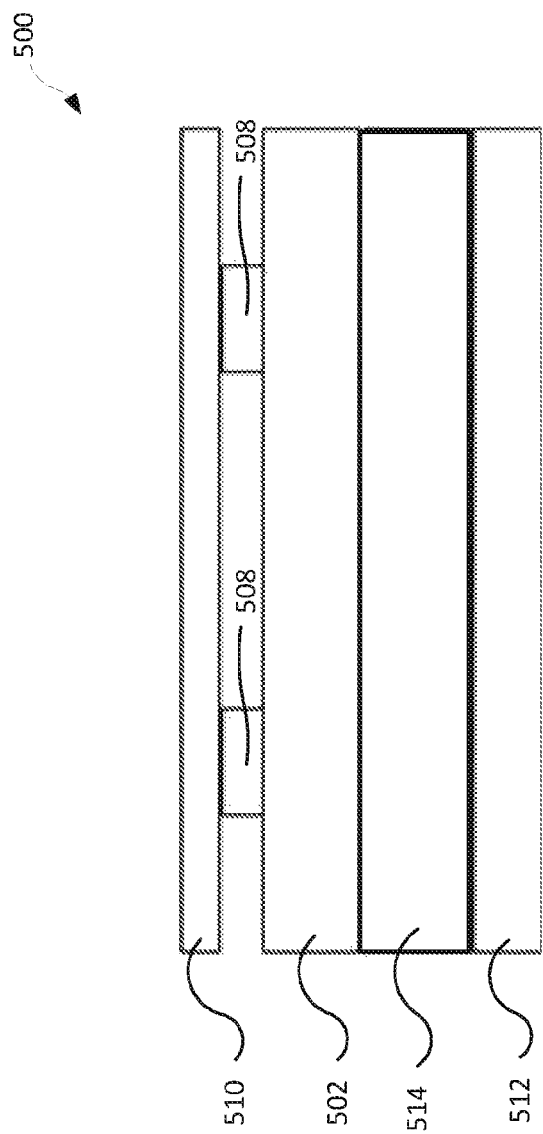

FIG. 5 depicts a side view of a sensor device 500 having a different fabric arrangement according to one example. The sensor device 500 again includes a substrate 502 and a plurality of sensor structures 508. The sensor device 500 further includes a flexible adhesive layer 510 and a fabric layer 514 worn by a subject 512. The flexible adhesive layer 510 is again disposed outward of the plurality of sensor structures 508. In this case, the fabric layer is disposed between the substrate 502 and the skin of the subject 512. The flexible adhesive layer may extend across a lateral extent of the substrate 502 and across a lateral extent of the fabric 514. The flexible adhesive layer 510 is configured to adhere the sensor device 500 to the fabric 514.

Figure 6:
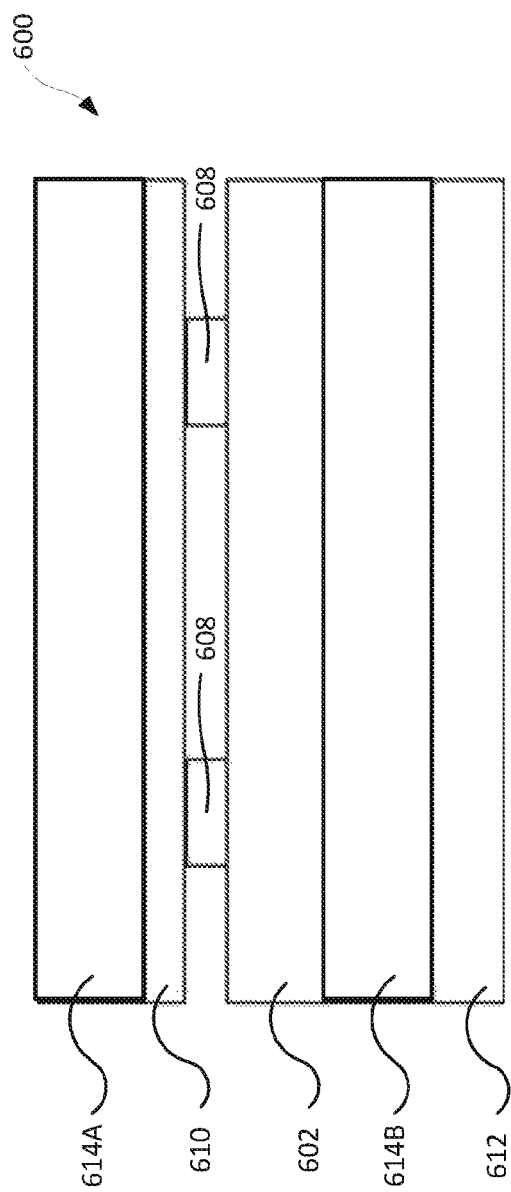

FIG. 6 depicts a side view of a sensor device 600 having a multiple-fabric layer arrangement according to one example. In this example, the sensor device 600 again includes a substrate 602, a plurality of sensor structures 608, and a flexible adhesive layer 610. In this case, a pair of fabric layers 614A and 614B are disposed on either side of the functional layers of the sensor device 600. The flexible adhesive layer 610 is disposed between the fabric layer 614A and the plurality of sensor structures 608. The substrate 602 is disposed between the plurality of sensor structures 608 and the fabric layer 614B. The fabric layer 614B is disposed between the substrate 602 and the subject 612. The flexible adhesive layer 610 is configured to adhere the sensor device 600 to the fabric layers 614A and 614B.

Figure 7:
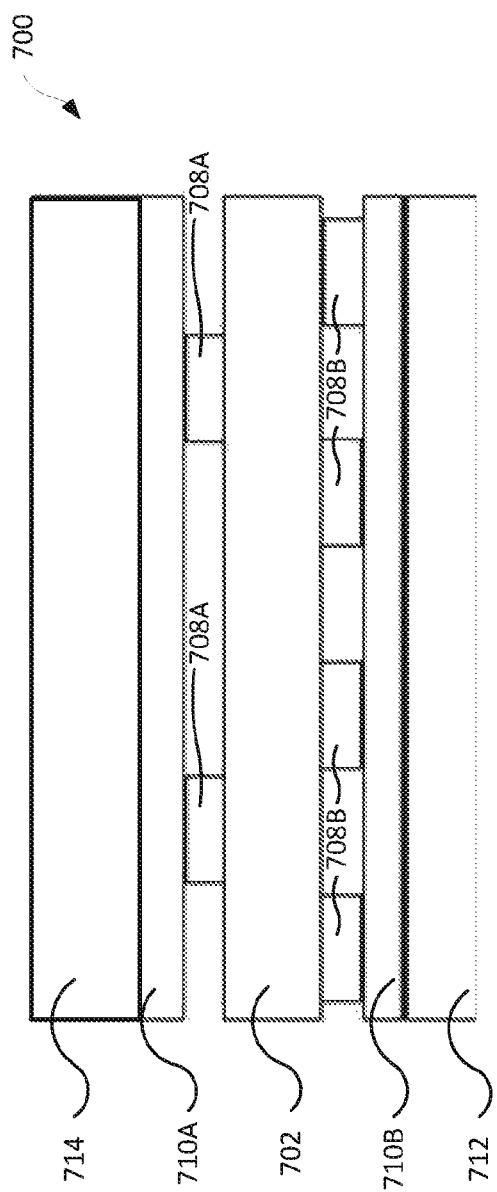

FIG. 7 depicts a side view of a sensor device 700 according to an example having a double-sided substrate arrangement. In this example, the sensor device 700 again includes a substrate 702 and sensor structures 708A, 708B. The sensor device 700 further includes a plurality of flexible adhesive layer 710A and 710B and a fabric layer 714. In this embodiment, a subject 712 wears the fabric layer 714. The flexible adhesive layer 710A is disposed between the fabric layer 714 and the plurality of sensor structures 708A. In this case, the sensor structures 708A and 708B are supported on opposite sides of the substrate 702. The flexible adhesive layer 710B is disposed between the sensor structures 708 B and the subject 712.

Figure 8:
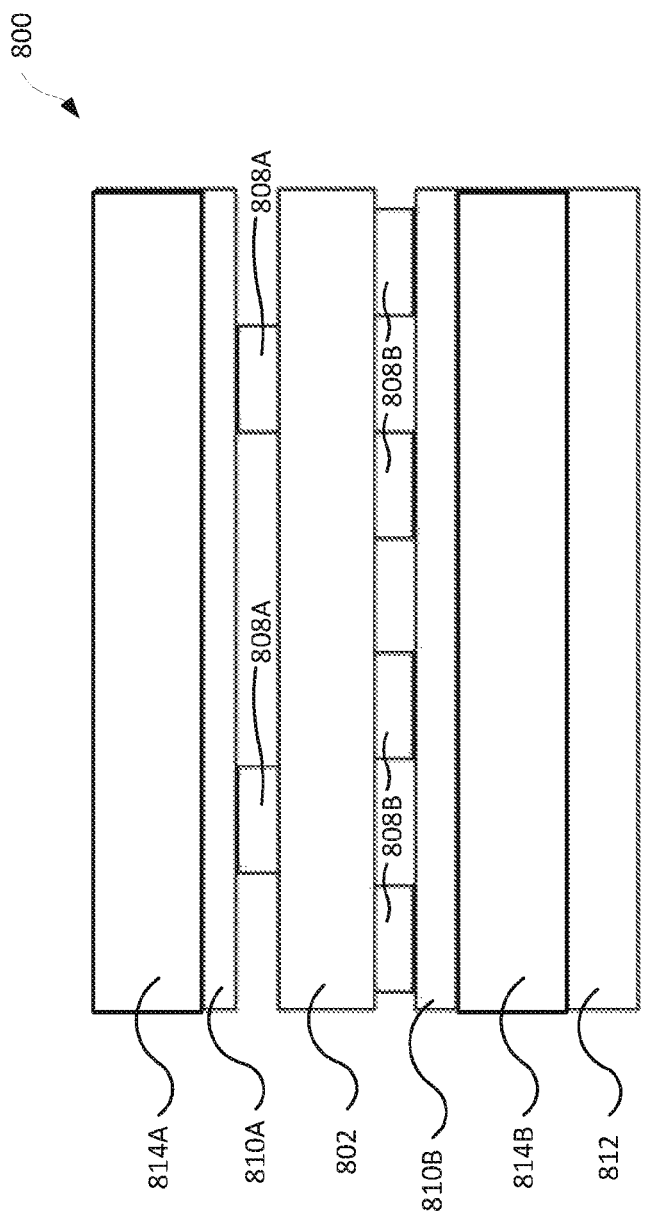

FIG. 8 depicts a side view of a sensor device 800 according to another example having a double-sided substrate arrangement. In this example, the sensor device 800 includes a substrate 802 and a plurality of sensor structures 808A and 808B. The plurality of sensor structures 808A and 808B are disposed on opposite sides of the substrate 802. The sensor device 800 further includes a plurality of flexible adhesive layer 810A and 810B. The sensor device 800 also includes a plurality of fabric layers 814A and 814B. In this case, the flexible adhesive layer 810A is disposed between the fabric layer 814A and the plurality of sensor structures 808A. The substrate 802 is disposed between the plurality of sensor structures 808A and 808B. The flexible adhesive layer 810B is disposed between the plurality of sensor structures 808B and the fabric layer 814B. The fabric layer 814B is disposed between the flexible adhesive layer 810B and the skin of the subject 812.

Figure 9:
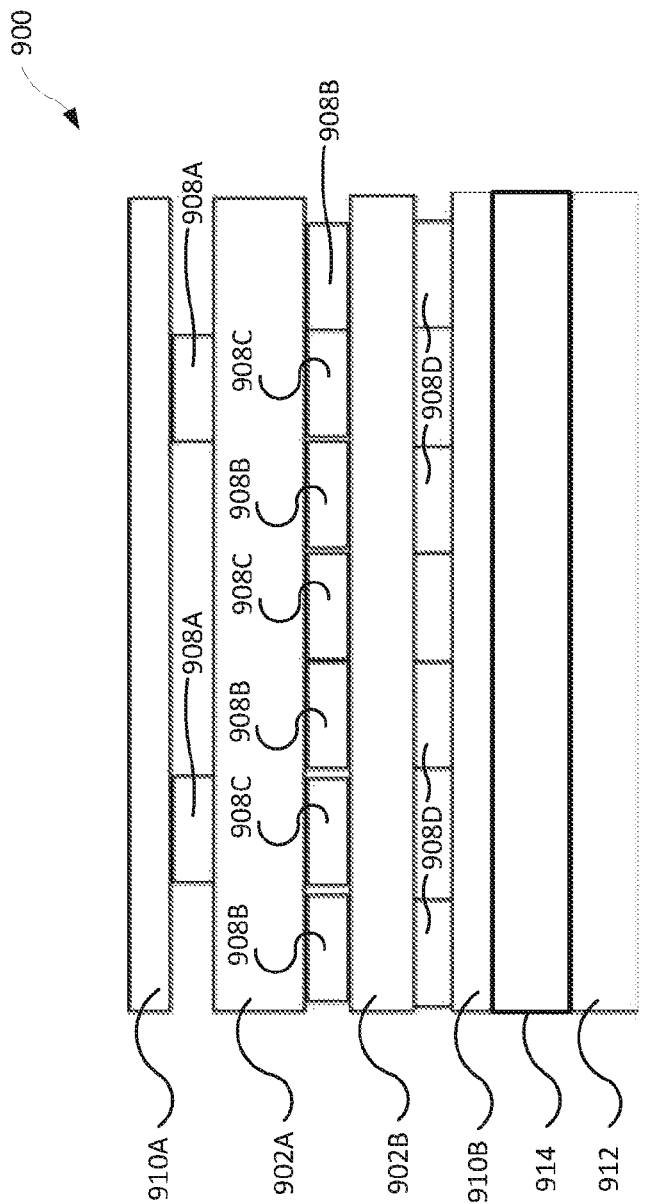

FIG. 9 depicts a side view of a sensor device 900 according to an example having a multiple substrates. In this example, the sensor device 900 includes a plurality of substrates 902A and 902B and a plurality of sensor structures 908A, 908B, 908C, and 908D. The plurality of sensor structures 908A are supported by the substrate 902A. The plurality of sensor structures 908B and 908C are supported by both substrate 902A and substrate 902B. The plurality of sensor structures 908D are supported by the substrate 902B. The sensor device 900 further includes a plurality of flexible adhesive layers 910A and 910B and a fabric layer 914. In this embodiment, a subject 912 wears the fabric layer 914. The flexible adhesive layer 910A is disposed above the plurality of sensor structures 908A. The flexible adhesive layer 910B is disposed between the plurality of sensor structures 908D and the fabric layer 914. The substrate 902A is disposed between the plurality of sensor structures 908A and the plurality of sensor structures 908B and 908C. The substrate 902B is disposed between the plurality of sensor structures 908B and C and the plurality of sensor structures 908D.

Figure 10:
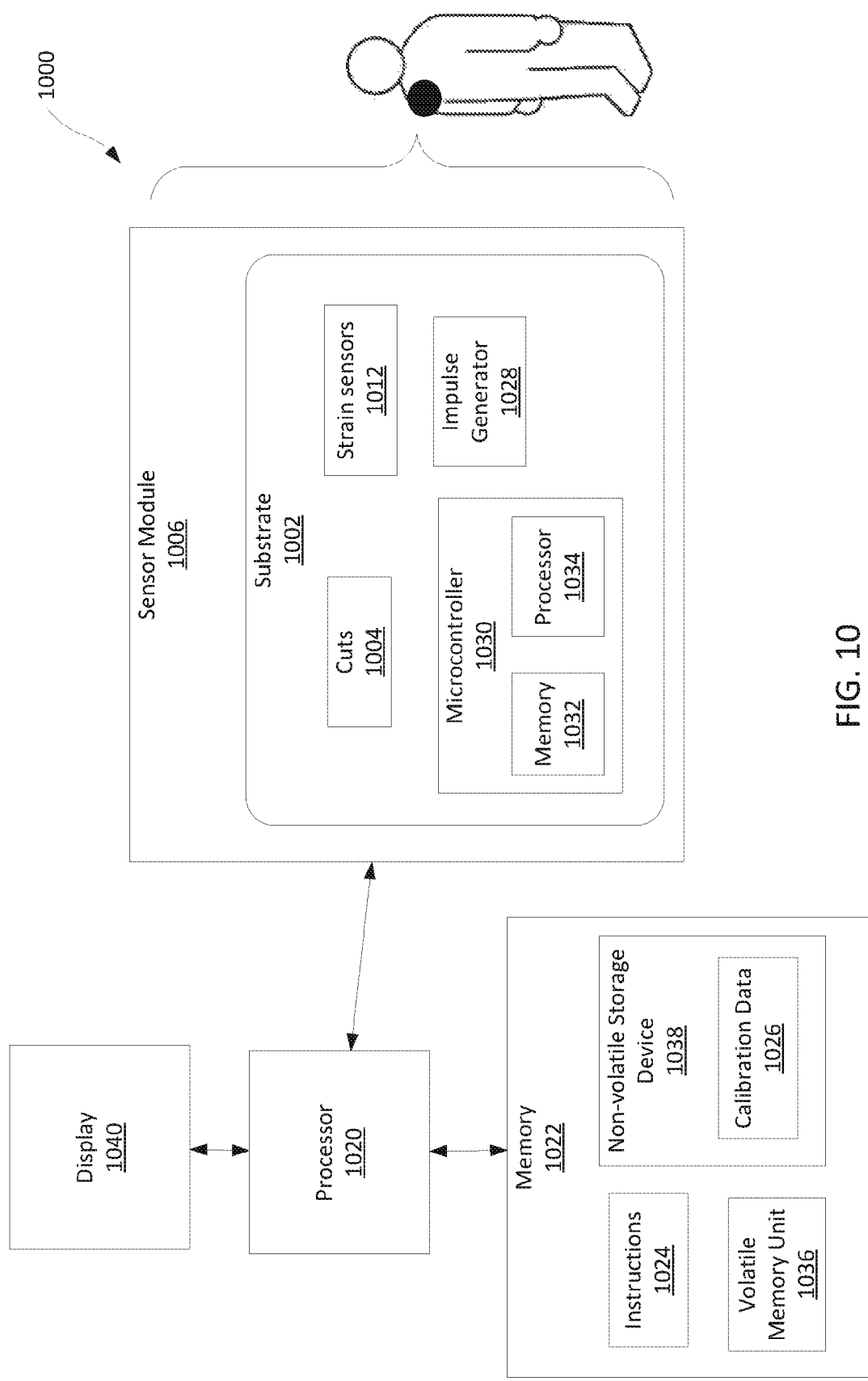
FIG. 10 is a block diagram of a kirigami-based sensor system in accordance with one example.

FIG. 10 is a block diagram of a kirigami-based sensor system 1000 in which the sensor devices described herein may be deployed. The system 1000 may be directed to capturing and using data indicative of deformation and/or displacement of a surface in connection with a wide variety of applications.

The sensor system 1000 includes a sensor module 1006 that may be configured in accordance with any of the examples described herein. As described above, the sensor module 1006 includes a flexible substrate 1002 having a number of cuts 1004 to define a kirigami structure. The sensor module 1006 further includes a number of strain sensors 1012. The strain sensors 1012 are supported by the flexible substrate 1002. Each strain sensor 1012 is disposed at a respective location across the kirigami structure.

The sensor system 1000 includes a processor 1020 and a memory 1022 in which instructions for configuring the processor 1020 are stored. The memory 1022 may be or include one or more memories. For example, the memory 1022 may include both volatile memory and non-volatile storage. Tracking instructions and calibration data are stored in the memory. Execution of the tracking instructions by the processor 1020 causes the processor 1020 to generate data indicative of displacement of the sensor module 1006 based on the calibration data and output signals from the strain sensors 1012. The data generated by the processor may be provided to a user on a display 1040 as described below.

In some cases, some of the data processing is implemented by a microcontroller or other processor integrated with the sensor module. As shown in FIG. 10, the sensor module may include a microcontroller 1030 supported by the flexible substrate 1002. The microcontroller 1030 may include a processor 1034 and a memory 1032 on which similar tracking and/or other instructions are stored.

Figure 11:
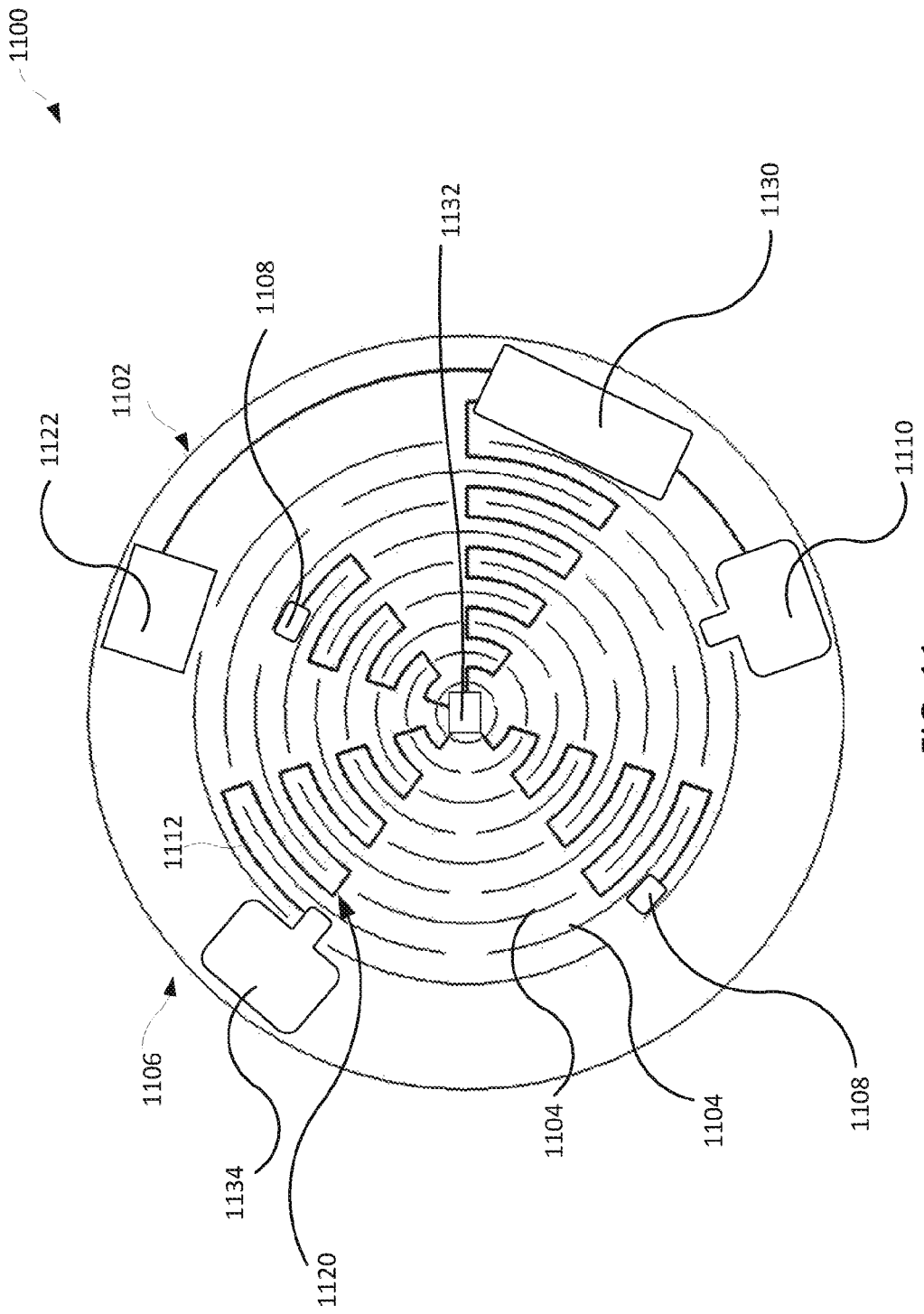
FIG. 11 is a schematic, plan view of a kirigami-based sensor system in accordance with one example in which processing and other non-sensor elements of the sensor system are supported by a sensor module.

FIG. 11 depicts a schematic, plan view of a kirigami-based sensor device 1100 in which a number of sensing, processing, and other components are integrated in accordance with one example. In this example, a plurality of sensor structures 1108 are disposed in a circuit 1122. The circuit 1122 includes a lead 1112 supported by a substrate 1102 and routed between the adjacent cuts of a plurality of cuts 1104. In this example, the number of cuts 1104 and the geometry dictate the wiring path along the substrate 1102.

The circuit 1120 further includes a power source 1122. The power source 1122 is supported by the substrate 1102. The power source 1122 is disposed adjacent to the ends of a pair of the plurality of cuts 1104. The circuit 1120 may be powered by in some cases via thermoelectric energy harvesting, a battery, electromagnetic induction, organic photovoltaic cells, and piezoelectric energy harvesting.

The circuit 1120 includes a microcontroller 1130 supported by the substrate 1102 and disposed adjacent to the ends of a pair of the plurality of cuts 1104. The circuit 1120 further includes an impulse generator 1132 supported by the substrate 1102 and disposed adjacent to ends of a pair of the plurality of cuts 1104. The circuit 1120 may also include one or more instrument amplifiers 1134 and other circuit elements to support data processing, data communications, and other functions.

Figure 12:
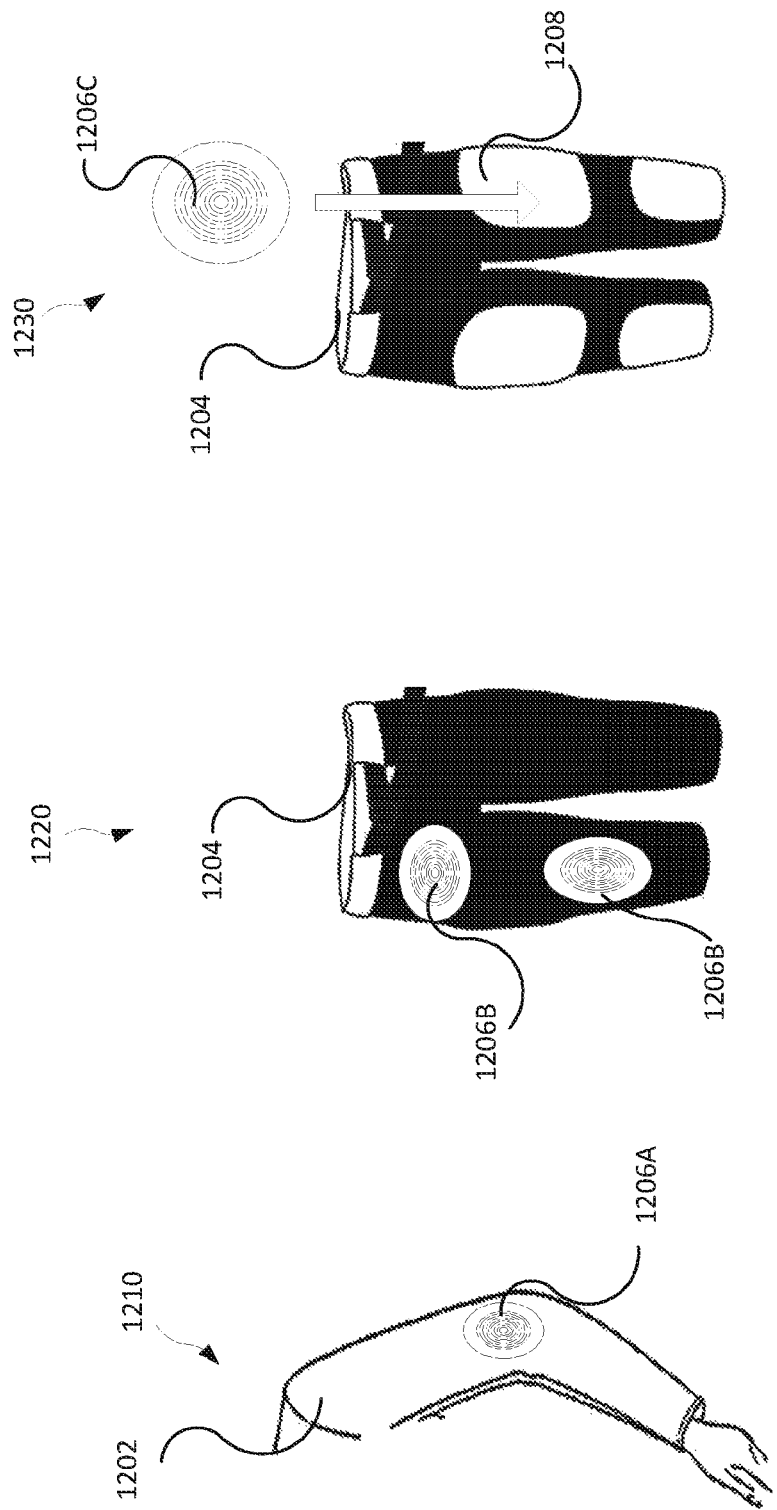
FIGS. 12-14 are schematic views of kirigami-based sensor systems in which a sensor device is integrated into a compression sleeve or other garment, protective equipment, joint brace, or other wearable item in accordance with several examples.
Figure 13:
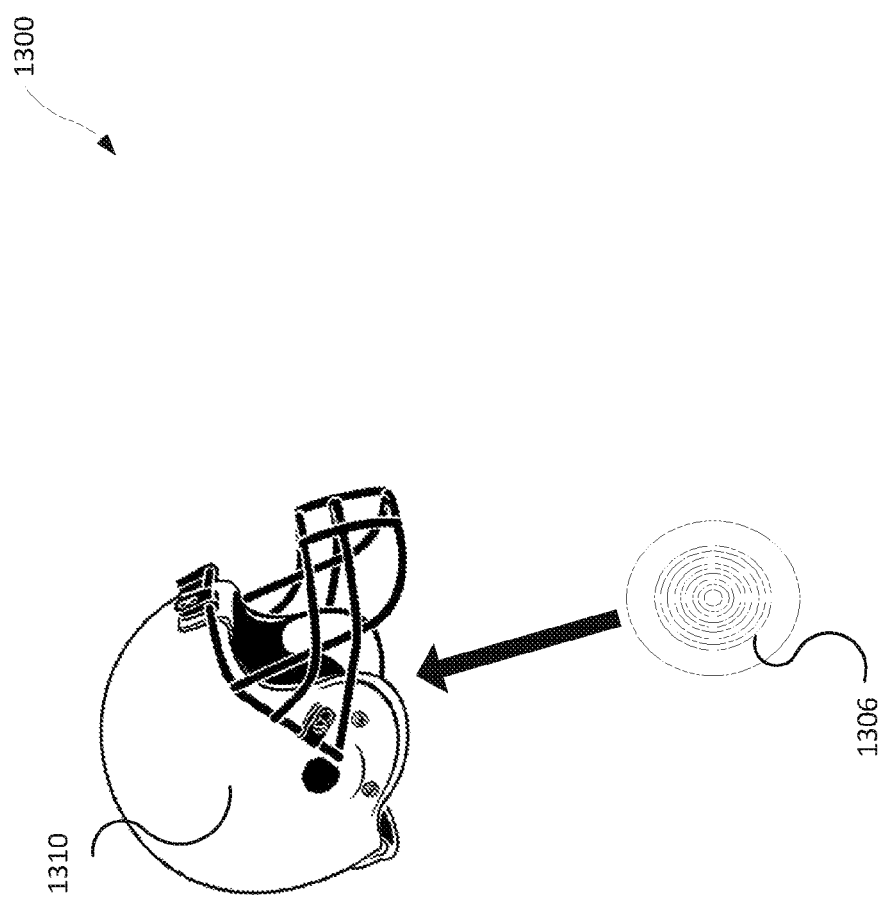
Figure 14:
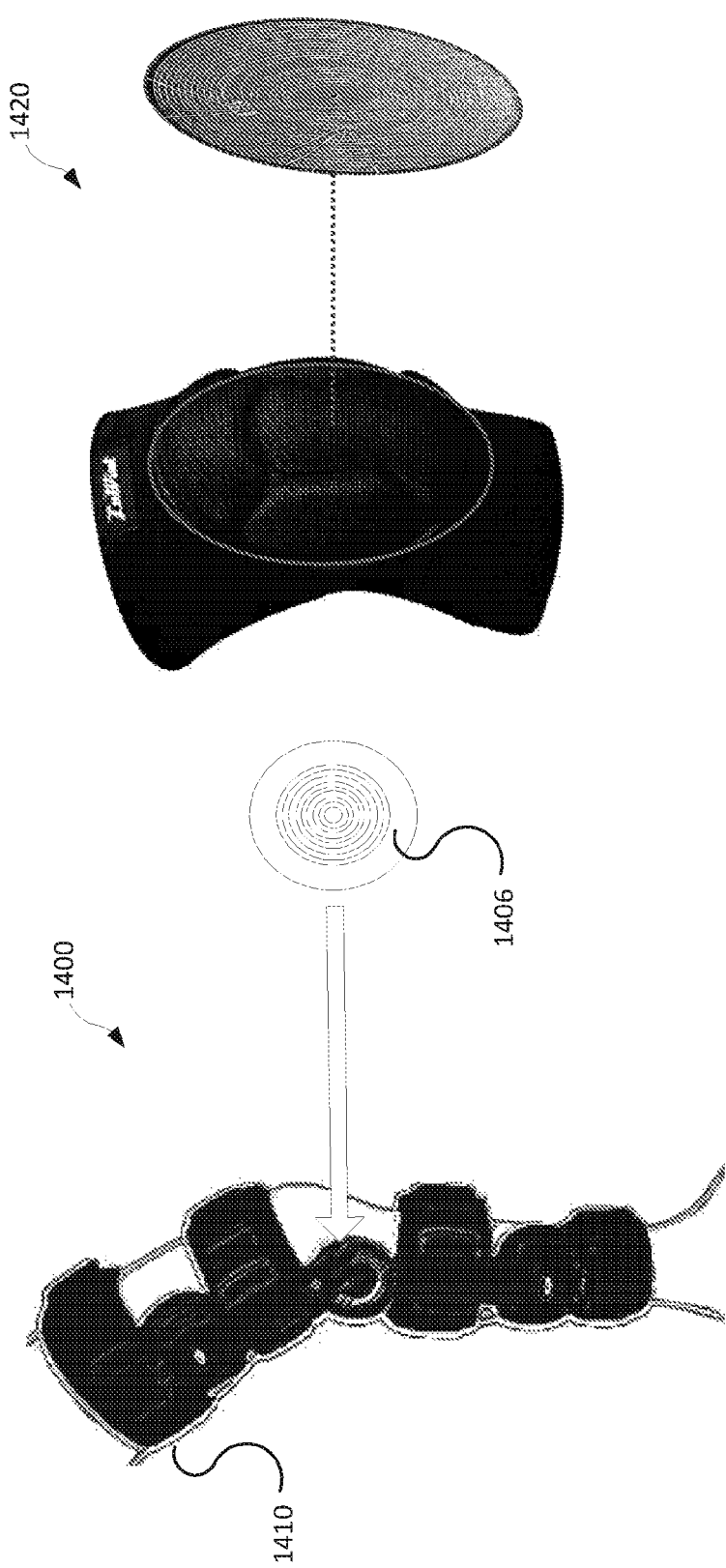

FIGS. 12-14 depict schematic views of kirigami-based sensor devices in which a kirigami sensor module 1206 is integrated into a compression sleeve 1202 or other garment, protective equipment, joint brace, or other wearable item in accordance with several examples. The sensor module may be configured in accordance with any of the examples described herein. The kirigami-based sensor devices may include bandages or patches adhered to the garment or skin, inserted in pockets, sewn into fabrics having electrically conductive fibers or flexible printed circuit fabric. The kirigami-based sensor device may include a garment in which the sensor module 1206 is integrated. The sensor module 1206 may also include an adhesive layer configured to adhere the sensor module 1206 to a subject. The sensor module 1206 may thus be a wearable module such that the displacement of a sensor module 1206 is representative of a three-dimensional curvature of a surface of the subject wearing the sensor module.

FIG. 12 depicts a schematic view of a kirigami-based sensor system 1210. The sensor system 1210 has a compression sleeve 1202 and a sensor module 1206A. The compression sleeve may be worn by a user. The sensor module 1206 may be adhered to the compression sleeve 1202 by an adhesive layer (not shown) to the compression arm sleeve 1202. Alternatively, the sensor module 1206A may be sewn in to the compression arm sleeve 1202. FIG. 12 further depicts a kirigami-based sensor system 1220. The sensor system 1220 has a pant 1204A and a sensor module 1206B. The sensor device 1200B may be sewn or attached to the pant 1204A. Also, the sensor device 1206B may be placed over or underneath the pant 1204A. FIG. 12 also shows a kirigami-based sensor system 1230. The sensor system 1230 has a pant 1204B and a sensor device 1200C. The sensor device 1200C may be inserted into the pocket 1208 of the pant 1204B.

FIG. 13 depicts a schematic view of a kirigami-based sensor system 1300. The sensor system 1300 may include a protective equipment 1310 configured to be worn by a user and a sensor module 1306. The sensor module 1306 is integrated into the protective equipment 1310. Examples of the protective equipment 1310 may include helmets, caps, and pads, etc.

FIG. 14 depicts schematic views of kirigami-based sensor systems 1400, 1420. The sensor system 1400 includes a post-operational knee brace 1410 and a sensor module 1406. The sensor module 1406 is embedded into the knee brace 1410 on the sides of knee brace, commonly used for anterior cruciate ligament (ACL) injuries. The sensor system 1420 provides another example of a knee brace. The sensor system 1420 includes a knee pad with a sensor module integrated therein. In these and other cases, the cuts of the kirigami module may be arranged according to the topography of the joint (or other object). The cut arrangement and the stiffness of the substrate are tunable. Therefore, sensor systems in the form of a tunable brace provide support to regions that need to be immobilized, yet flexible enough to prevent disuse atrophy, all the while capable of sensing the positions of the knee and other vital parameters. Other examples may include the sensor module 1406 placed within the scaffold of a fabric knee sleeve, or integrated throughout the entire knee brace.

Figure 15:
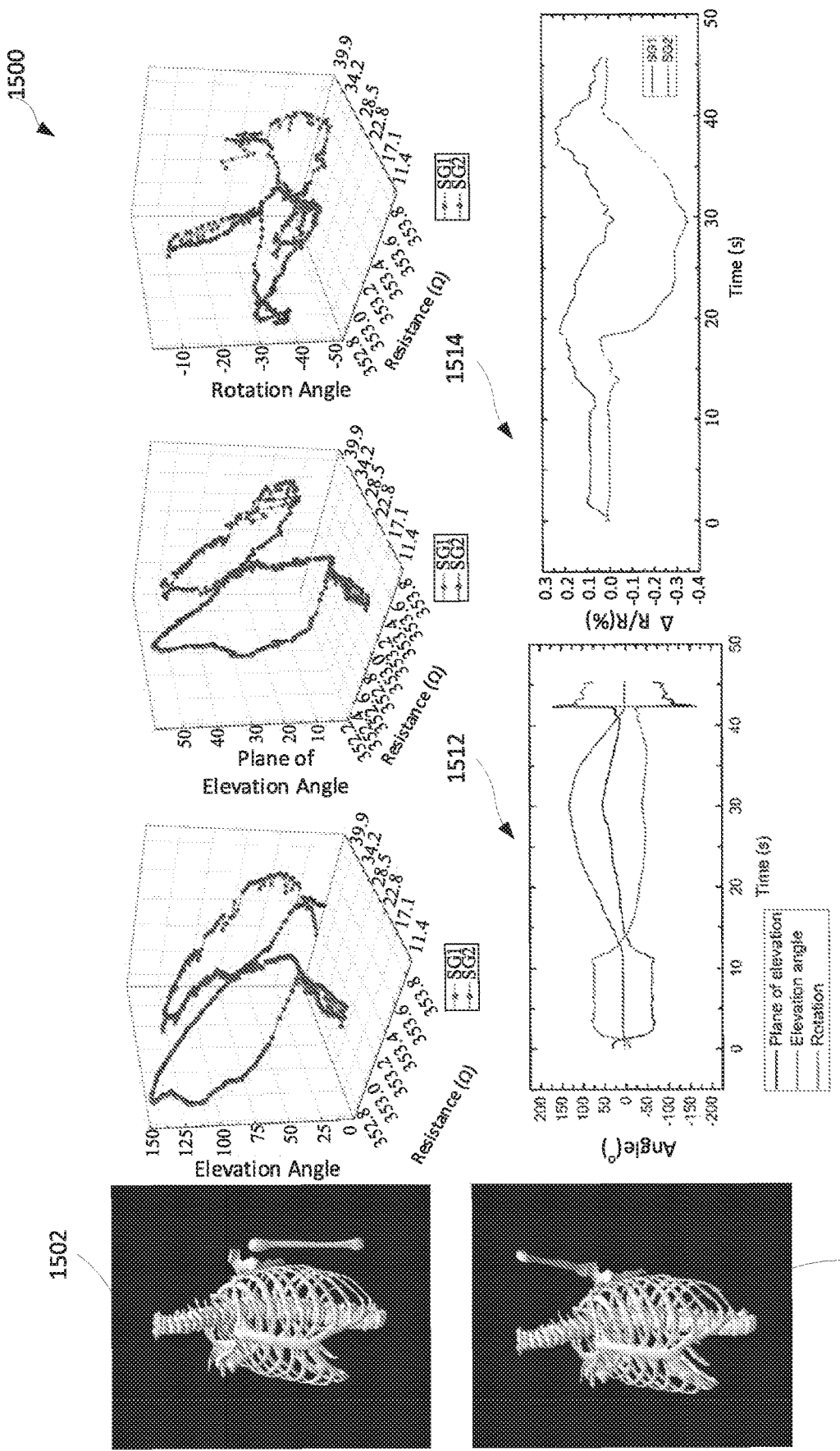
FIG. 15 are plots of data generated by an example kirigami sensing module tracking angular positions of a shoulder in accordance with one example.

FIG. 15 depicts the results of the kirigami sensing module 1206 for tracking angular positions of the shoulder. An example is a continuous measurement of raising the user's arm. FIG. 15 shows a skeleton 1502 in neutral position. FIG. 15 also shows a skeleton 1504 with an arm raised up. The graphs 1500 show elevation angle, plane of elevation angle, and rotational angle are plotted against resistance, measured using a measurement apparatus (e.g. semiconductor parameter analyzer, multimeter, Arduino (™) module, a miniaturized integrated source measurement unit, etc.). The scatter plots represent data from two strain gauges SG1, SG2 as the shoulder moves from one position to the other. A plot 1512 shows the angular position versus time. A plot 1514 shows the change in measured electrical resistance versus time.

Figure 16:
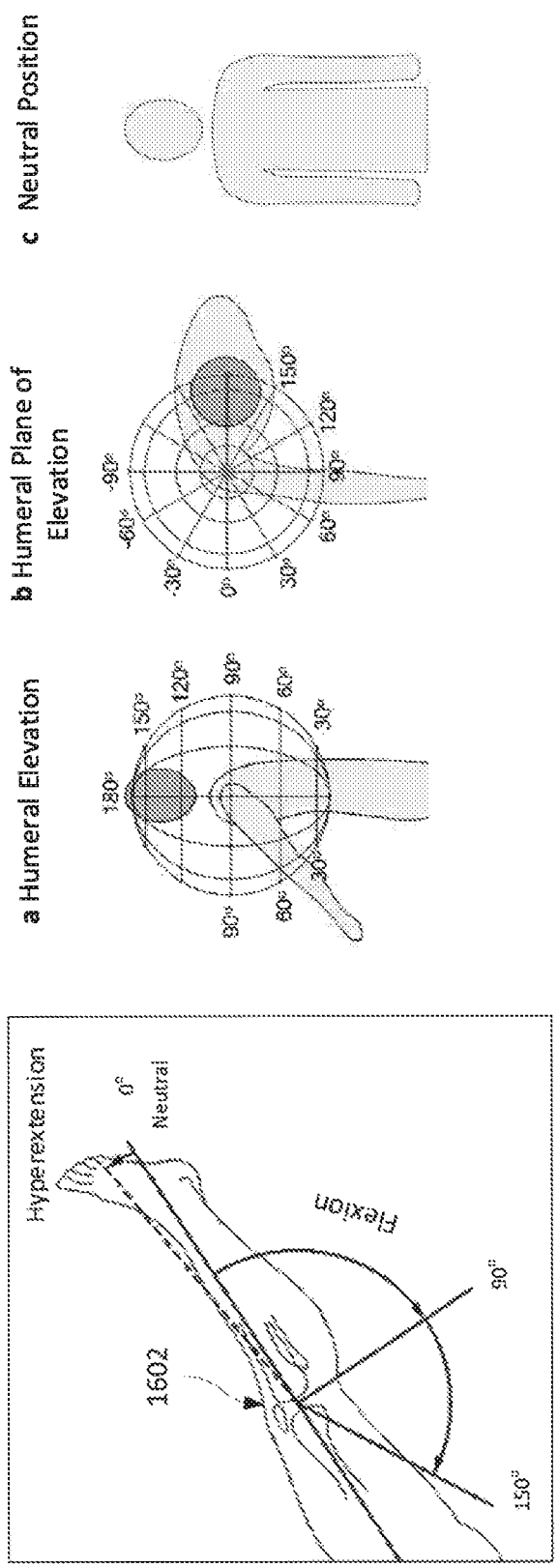
FIGS. 16-19 are flow and other diagrams of procedures implemented by kirigami-based sensor systems in accordance with several examples.

FIGS. 16-19 are flow and other diagrams indicative of procedures implemented by kirigami-based sensor systems in accordance with several examples. The kirigami-based sensor systems described herein provide a customizable platform for the collection of data using a number and a variety of sensor structures suited to different applications. For example, FIG. 16 depicts coordinate systems used to define angular positions of the body for lower and upper limbs. The origin is located at the center of the shoulder and the humeral elevation angle represents the plane to the side of the person. The humeral plane of elevation is the plane from the top view of the person, most referred to as the transverse plane. The neutral position is associated with a standing position as shown. Not shown but equally important is a third axis relating to the rotation of the shoulder joint. This coordinate system may also be applied to other body joints. To measure the range of motion of the knee, the shoulder, or other joint, the kirigami-based sensor system allows the placement of sophisticated but substantially rigid sensor structures dynamically in three dimensions when worn on the subject.

Figure 17:
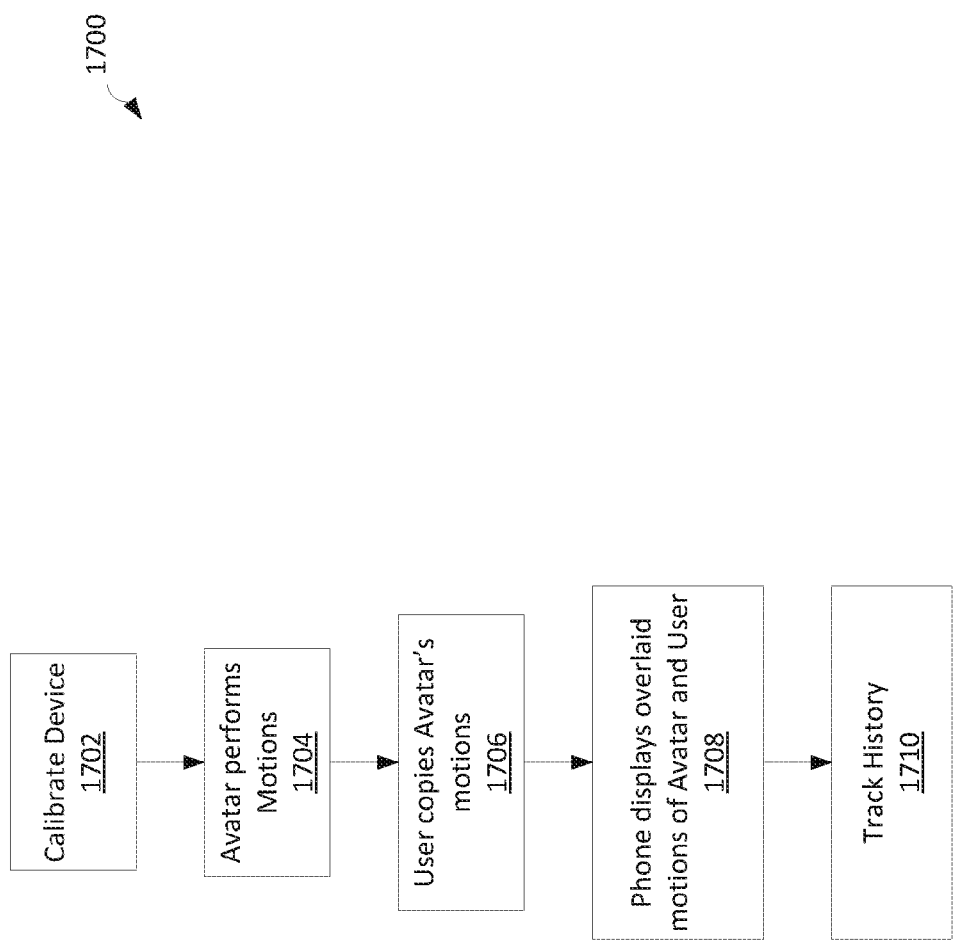

FIG. 17 depicts a flow diagram 1700 of procedures implemented by kirigami-based sensor systems in accordance with several examples. The procedures may be implemented via execution of one or more of the above-described instruction sets by one or more of the above-described processors. In some cases, a range of motion of a subject wearing the sensor module may be determined. Alternatively or additionally, an activity type in which a subject wearing the sensor module is engaged may be determined via pattern analysis of the data indicative of the displacement.

To aid in the use of the kirigami-based sensor system to improve physical therapy, achieve desired athletic performance, or for other desired purposes, integration with substantially real time visualization and/or feedback on motion may be used. Thus, one implementation of the kirigami-based sensor system includes communication with a virtual reality headset and/or augmented reality platform (e.g. Apple AR Kit) to provide instruction and feedback to the user on how to perform certain motions for daily activities, physical therapy exercises, weight-lifting, stretching, yoga, etc. To aid with this implementation, a smartphone app is used to provide real-time motion analysis to the user based on exercises prescribed by a physiotherapist. The smartphone app ascertains the orientation and extent of the imaged environment (e.g. a room), and an avatar is substantially superimposed on the captured image of the subject. The avatar then performs a motion, for instance, raising the arm along the elevation angle plane. The phone displays the overlaid motions of the avatar and the user. The user is instructed to perform the same motion, while the worn kirigami module tracks the position. Deviations from intended motion are highlighted on the screen (and/or trigger sounds, and/or haptic feedback). The user is then provided with an assessment of progress over time in achieving desired range of motion.

The flow diagram 1700 depicts the integration of the kirigami module with handheld devices for augmented reality applications. In step 1702, the mobile device is calibrated based on the room and direction of the phone held, to which an avatar is placed in the room and performs a motion. In step 1704, the user then copies the avatar's motion, while the phone simultaneously gives feedback to the user on his/her performance. After the full motion is performed, in step 1708, the phone displays the motion captured by the avatar, the ideal motion, overlaid with the motions performed by the user. In step 1710, real-time feedback and tracking history is provided to ensure proper performance. This is useful to reap the full benefits of the activities or prevention of injuries, such as when performing physiotherapeutic exercises. Existing implementations of AR mobile devices to track positions are largely limited to the positions that are trackable based on where and how the phone is held and provides no other functionality.

Figure 18:
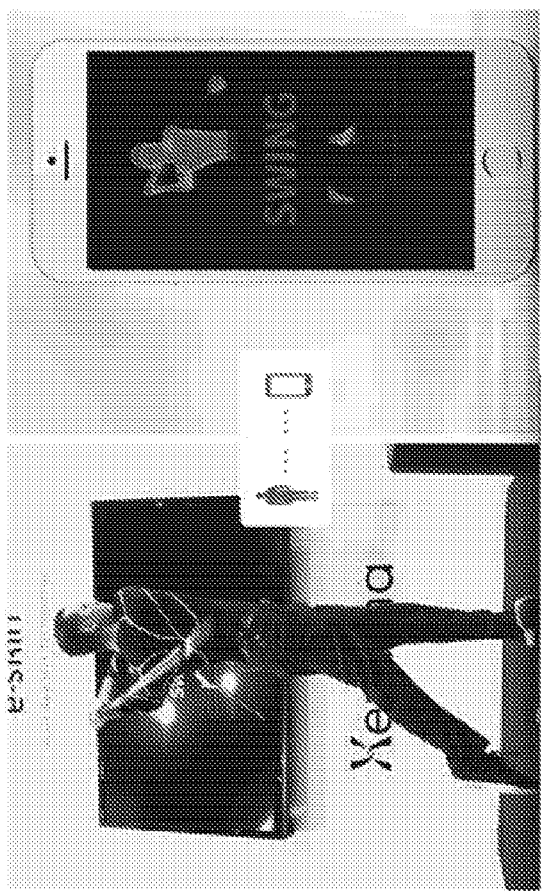
Figure 18:
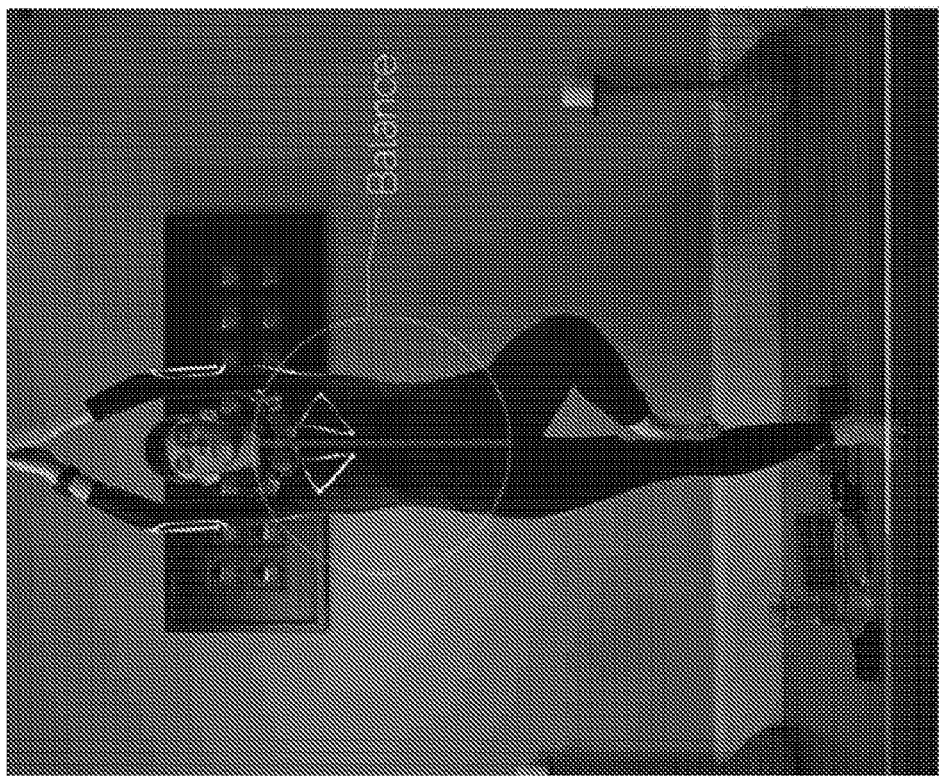

FIG. 18 shows another use of the kirigami module involving the correction of posture during activities, such as performing yoga or swinging a golf club. The sensors in the module communicate with the mobile device and provide real-time feedback with audio and visual cues to the user to ensure proper positioning. The camera on the mobile device is positioned in front of the user and the data is recorded and presented via Bluetooth, near field communications, etc.

Another example use of the kirigami module provides real-time feedback for weight-lifting and other activities. For instance, feedback may be provided to ensure proper form while squatting. An avatar performing the same position is shown to the user in the form of a head-mounted display or in another implementation in the form of smart spectacles through mixed reality VR/AR. A smartwatch then collects the data and gives visual and haptic feedback to the user while he/she is performing the motion.

Figure 19:
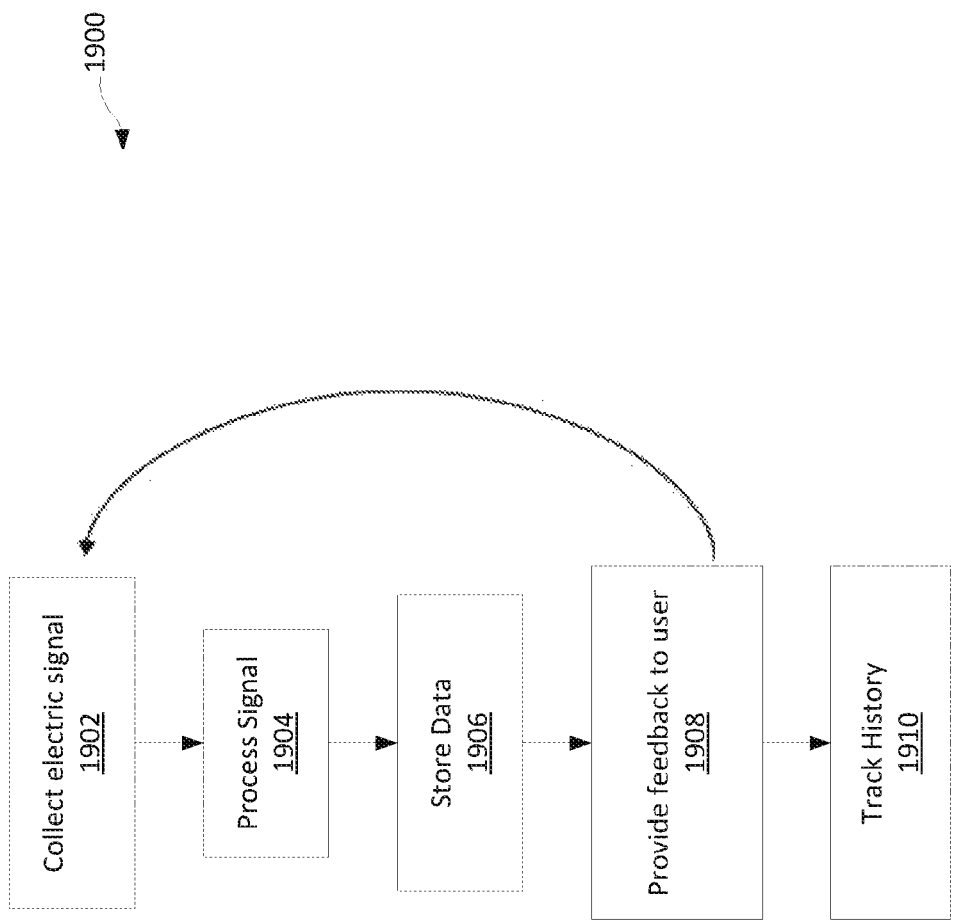
Figure 20:
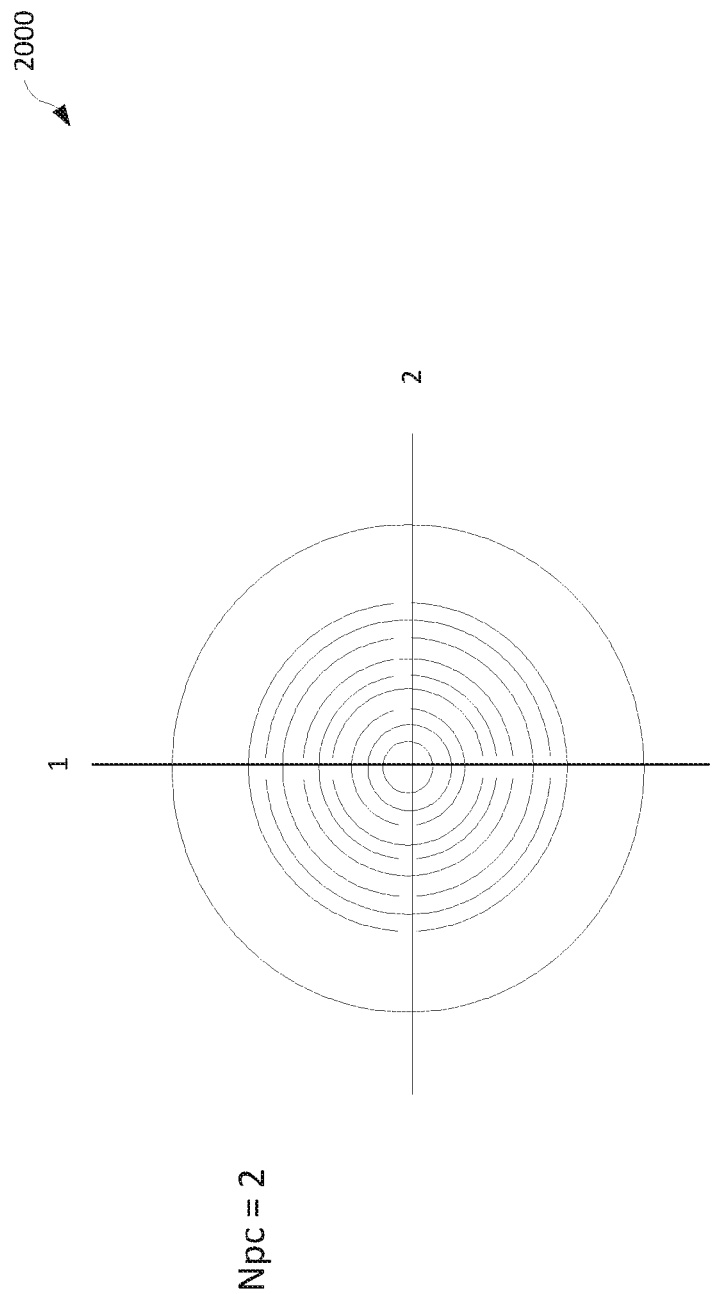
FIGS. 20-23 are schematic plan views of kirigami structures with various cut patterns in accordance with a number of examples.
Figure 21:
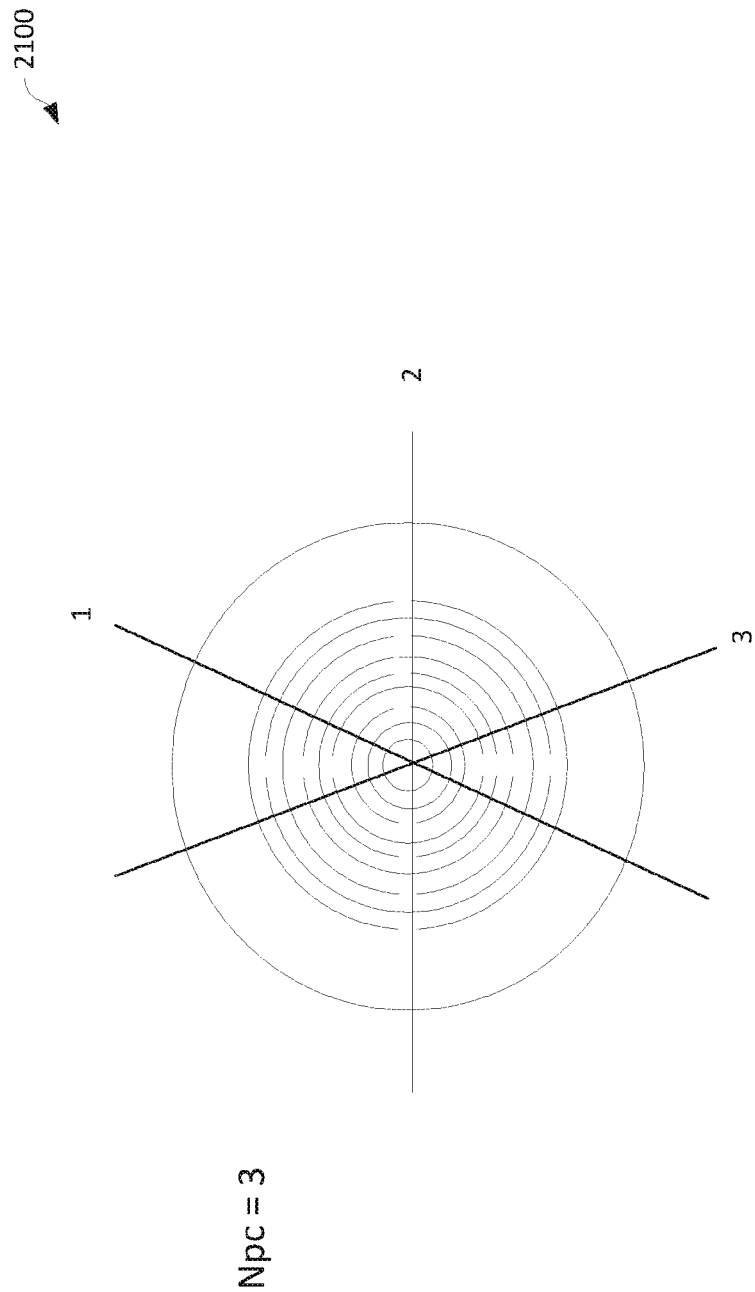
Figure 22:
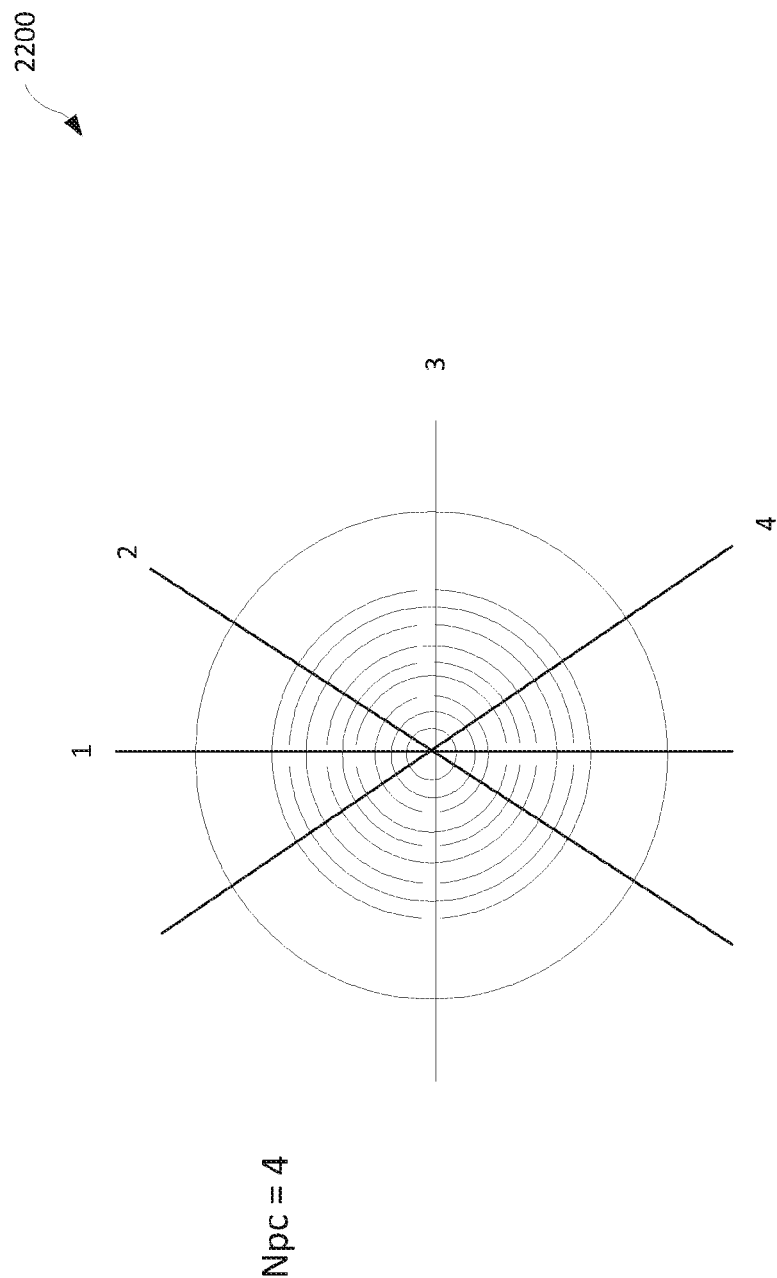
Figure 23:
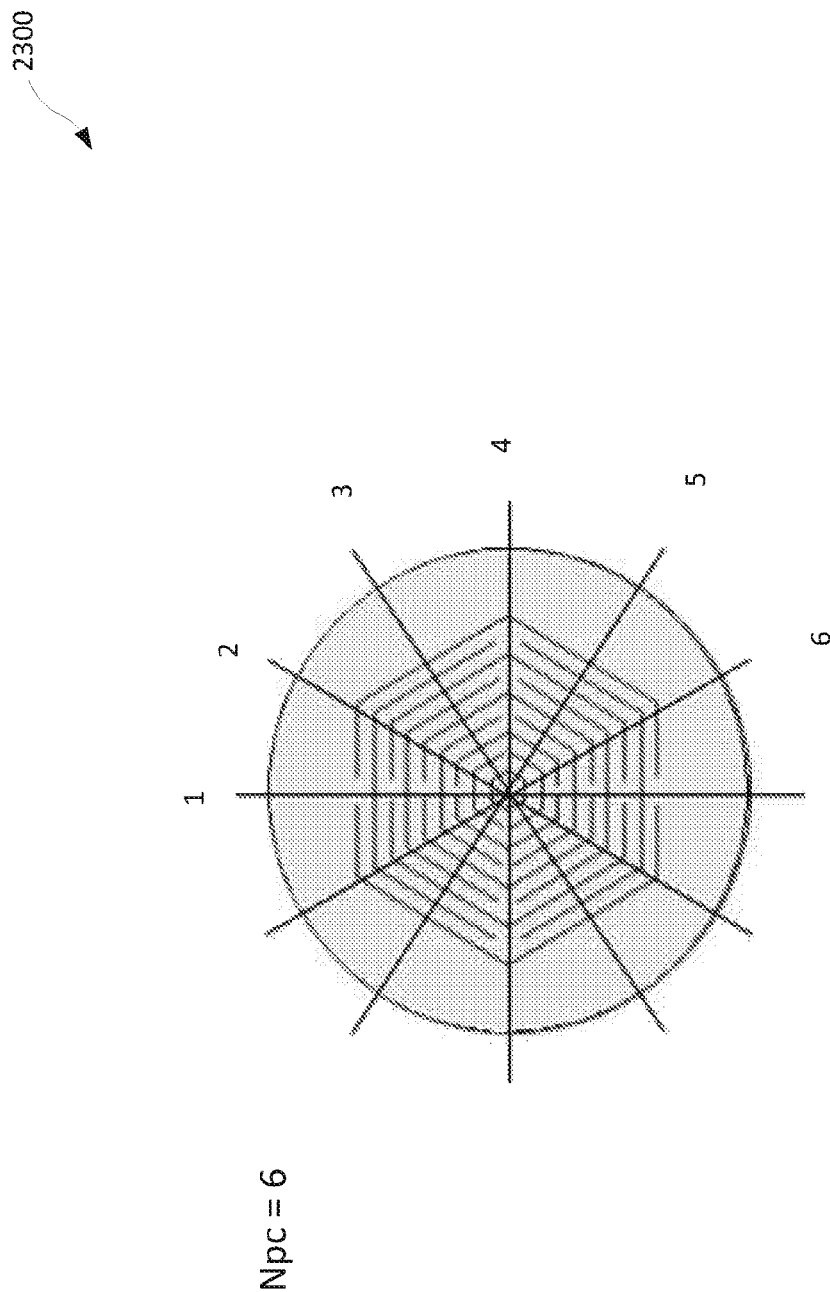
Figure 24:
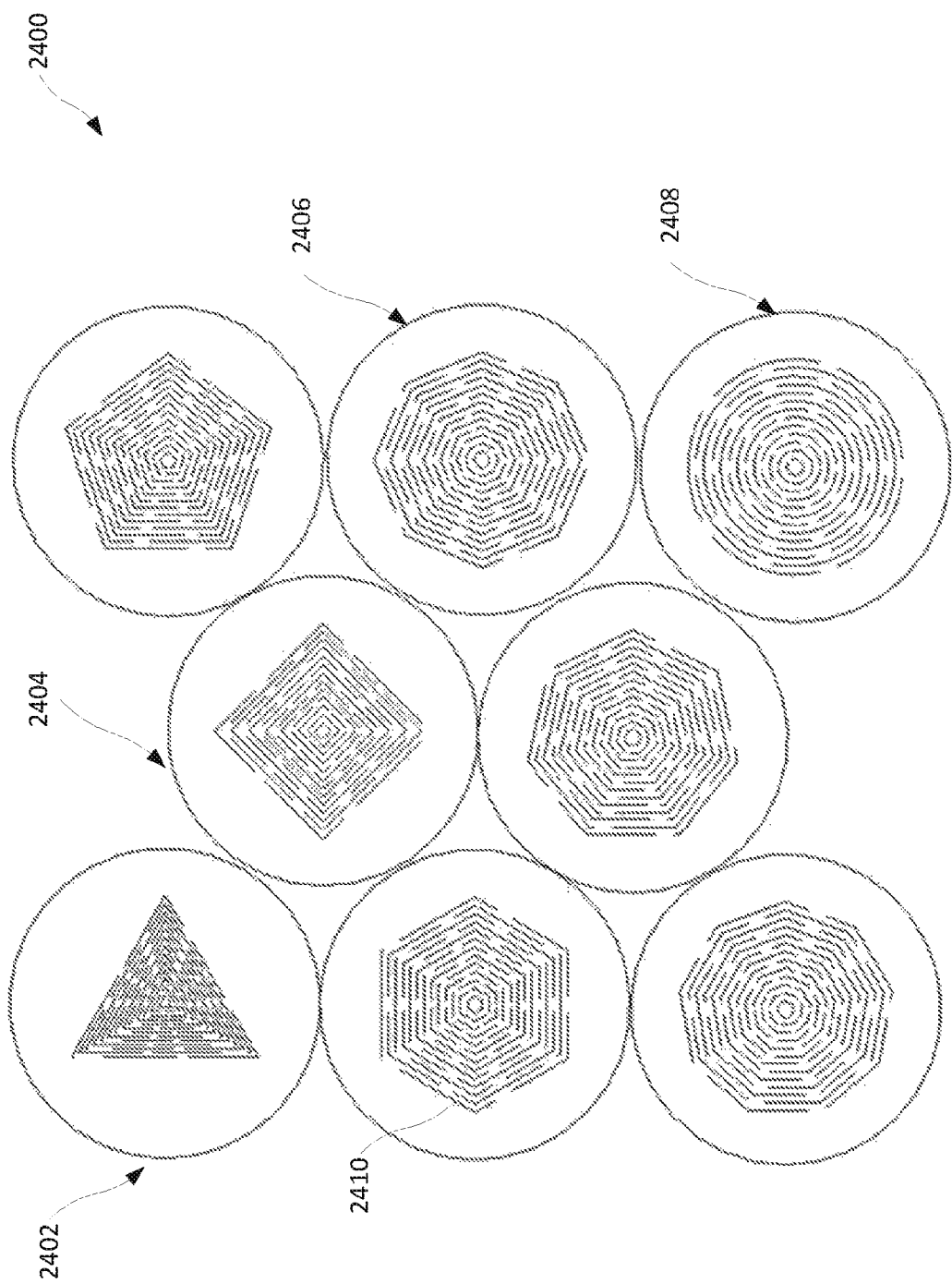
FIG. 24 is a schematic plan views of kirigami structures of various shapes in accordance with a number of examples.

FIG. 19 shows a flow diagram 1900 including steps directed to data collection for the above-described applications. In step 1902, electrical signals are collected from the sensor module. In step 1904, the signals are processed to generate data indicative of surface deformation and/or displacement. In step 1906, the generated data is stored. In step 1908, feedback is provided to the user based on the generated data. In step 1910, a history of the output may be tracked or otherwise maintained.

In some cases, the generated data is correlated with a subject's assessment of physical pain and/or strain. Such correlation may be useful in, for instance, determining trends in the subject's wellbeing, performance, etc. For example, the generated data may be used to evaluate when a tennis player executes a serve in a particular way that results in less (or more) shoulder pain, but there's an impact on the resulting ball speed and spin. The generated data in that example may alternatively or additionally be evaluated to assess whether ball speed is correlated with propensity for injury, proper technique, etc. The generated data may be useful in physical therapy (PT) contexts in which range of motion measurement in PT settings is done both until resistance is felt but also with regard to the level of pain felt at the extremes. Coaches or trainers may also use the generated data to detect an increase in range of motion in connection with pain, performance, or other monitoring. In some cases, the generated data may thus be used to correlate the sensation of pain with the tracked motion, as well as the results of such motion (e.g., ball trajectory, speed, and spin in tennis and other sport contexts). The generated data may be captured and/or aggregated over time (near or long term), which may be useful, for instance, in tracking a player's performance improvements (e.g., shot making and other efficacy measures). The generated data is useful in a wide variety of sports, including, for instance, baseball (e.g., pitching) and golf.

In other cases, the generated data may used to support the evaluation of the relationship between pain as the body's way to indicate discomfort within a particular joint together with the geometrical parameters of the joint itself. The generated data may be used to track that relationship, and thereby quantify the effective wear and tear on a joint. The generated data may thus improve upon past monitoring techniques, in which, for example, coaches count the number and speed of pitches thrown, while not knowing details of how the joints are actually engaged or moving, or the extent to which pain is being experienced.

FIGS. 20-25 show various examples of kirigami cut patterns. The cut patterns define kirigami beams based on the number of cuts along the perimeter. The outer border in these examples are circular, but the sheet may be cut into any shape. Generally, for symmetric cut patterns, as the number of cuts increase, so too does the order of rotational symmetry operations that apply to the structure. For instance, two cuts along the perimeter correspond to second order of symmetry, three cuts correspond to third order, four cuts correspond to fourth order and so on. Furthermore, the order of symmetry also corresponds to the number of sides created by straight lines formed in concentric patterns. For example, the hexagonal pattern has six sides, and so the hexagonal pattern has sixth order of symmetry. Upon deflection, the order of symmetry breaks.

FIG. 25 shows a schematic plan view of a kirigami-based sensor device 2500 having multiple connected kirigami structures configured for use as a shoe insert in accordance with one example. In this case, the kirigami module uses several different cut patterns at different regions of the foot to match the shape of a foot. Different kirigami patterns may be combined to fit the different regions of the foot.

FIG. 26 depicts a number of examples of rotationally symmetric kirigami modules. In these examples, the radial spacing (w), the angular spacing (φ), the number of cuts along the perimeter of each concentric circle ($N_{pc}$), as well as the thickness (t) and inner and outer diameters (Di and Do), are varied. In some cases, the modules are created by laser-cutting polyethylene terephthalate (PET) sheets of 90 micrometers in thickness. The Young's modulus and Poisson's ratio of the film is 2.2 GPa and 0.37, respectively. Each cut kirigami sheet is then deflected out of plane by 50 mm using a string attached in the middle of the module. Local and global stiffness of the kirigami module, for a given selection of substrate composition and thickness, is engineered through the geometry of the cuts. For instance, a greater number of cuts along the perimeter produces shorter beams with an overall higher stiffness. Longer and more closely spaced (e.g. smaller w) produces lower stiffness. Using different dimensions and symmetries of the cut patterns allows also to approximate complex surface curvatures better, such as the examples described herein to fit a human foot.

The examples of FIG. 26 illustrate how different cut patterns influence the deformed state. The first six examples (Examples a-f) are kirigami springs, while the last example (Example g) is a normal conical helix spring. The resulting kirigami springs are configured by radial spacing (w), angular spacing (φ), the number of cuts along the perimeter of each concentric circle ($N_{pc}$), as well as the thickness (t) and inner and outer diameters (Di and Do). Table 1 shows the parameters (e.g., geometric parameters) associated with the cut patterns illustrated. The difference between Example a and Examples b through d involves varying the parameters w, φ, and $N_{pc}$, respectively. The cut pattern in Example e differs from Example a in the parameters w, φ, and $N_{pc}$. Example f has nonequal radial spacings to demonstrate how different curvatures may be accommodated within the spring. For instance, strategically designing the radial spacing in accordance with the outer radius may result in a more cylindrical shape. Example g is a helical conical spring having one continuous cut, which does not exhibit local saddles. The extent to which each of the individual rings deflect within the kirigami structure is visually dissimilar especially with respect to the normal helical conical shape. The most notable difference between the kirigami springs and that of the helical spring is that, as the kirigami spring deflects, there is no torsional moment around the central axis.

TABLE 1

|   | Radial Spacing (w) [mm] | Angular Spacing (φ) [°] | Number of Cuts ($N_{pc}$) |
|---|---|---|---|
| a | 3 | 10 | 2 |
| b | 5 | 10 | 2 |
| c | 3 | 25 | 2 |
| d | 3 | 10 | 4 |
| e | 1 | 5 | 4 |
| f | Varies | 10 | 2 |
| g | 2 | — | 1 |

The mechanical responses of the kirigami springs were determined via uniaxial tensile tests. For example, an example with a PET substrate was sandwiched between two acrylic rings to ensure the outer boundary is fully constrained and then clamped into tensile grips via a 3D printed specimen holder. A probe was used to apply a uniaxial force at the center of the spring at a rate of 5 mm/s. Due to the limitations of the dimensions of the tensile tester, a maximum displacement of 70 mm was used; however, this is not the point of failure. FEA results were used to assume the point of failure for the baseline pattern (Example a of FIG. 26), showing a maximum displacement of the kirigami spring of around 160 mm at a maximum force of 6 N. At a displacement of around 55 mm, the spring started to behave non-linearly.

A ring model may be used to further illustrate the deformation behavior of the kirigami spring. Displacement increased as a function of increasing radius due to the greater degree of curvature. This creates a necking effect as demonstrated by the large displacement. The local strains, e.g., at the ends of the cuts, lead to plastic deformation and then to failure.

FIG. 27 depicts logarithmic plots of experimental force versus displacement for varying parameters w, φ, and $N_{pc}$ at a reduced size to overcome the experimental apparatus limitations. The first plot (a.) represents changes in the number of cuts along the perimeter, maintaining a constant angular and radial spacing. The second plot (b.) shows how increasing the angular spacing involves more force to deflect the spring. The third plot (c.) depicts how increasing the radial spacing increases the force involved to deflect the spring. This is due to the length of beams that are in bending. Regardless of the specific design changes whether $N_{pc}$, φ, and/or w, when the beams are shortened, more force is involved to achieve the same displacement. While the regimes are designated as linear or nonlinear, there is a third transient region, which is the onset of plastic deformation.

In examples involving strain gauges, the electrical resistance of the strain gauges changes as gauges are elongated and thus a voltage change is detected as the user moves the joint. The voltage change is then computed to determine the strain, which corresponds to the angular position. In some cases, rosette strain gauges are used, in which three strain gauges are stacked 0°, 45°, and 90°. The rosette strain gauge may be connected to a Wheatstone Bridge in a quarter bridge configuration to detect very small changes in the resistance, e.g., within milli-Ohms. The following equations may be used to determine the principal strain from the strain given from each strain gauge where ϵ represents strain.

$$\epsilon_0 = \frac{\epsilon_x + \epsilon_y}{2} + \frac{\epsilon_x - \epsilon_y}{2}$$
$$\epsilon_{45} = \frac{\epsilon_x + \epsilon_y}{2} + \frac{\gamma_{xy}}{2}$$
$$\epsilon_{90} = \frac{\epsilon_x + \epsilon_y}{2} - \frac{\epsilon_x - \epsilon_y}{2}$$

Therefore, $\epsilon_x = \epsilon_0$, $\epsilon_y = \epsilon_{90}$, and $\gamma_{xy} = 2\epsilon_{45} - (\epsilon_0 + \epsilon_{90})$.

FIG. 28 shows data from an example in which a kirigami module was used to measure angular positions of the shoulder during various motions. Three different shoulder motions are depicted, along with the resulting change in resistance and corresponding angular position. In each of these examples, a user is wearing a sensor configured as described herein. The user executes a motion while wearing the kirigami module with integrated sensors. The executed motion generates local deformations, sensed by the strain gauges as a change in electrical resistance, and captured by a control unit. A correlation may be made between the position of the limbs (and joint), and signals from the sensor(s). In this manner, the kirigami modules described herein may provide information about the movement of the joint.

FIG. 29 depicts a sensor device 2900 configured in accordance with one example. The sensor device 2900 may have a number of components and/or features in common with the devices described above. For instance, the sensor device 2900 includes a substrate 2902 having a plurality of cuts 2904 through the substrate 2902 to define a set of substrate sections, as described above. The substrate 2902 is flexible to allow deformation as described above. The sensor device 2900 includes a number of strain gauges 2906 supported by the substrate 2902. Alternative or additional strain sensors or other sensor structures may be included. As described above, deformation of the substrate 2902 deforms sections of the substrate 2902 such that each strain gauge 2906 provides an indication of the respective extent of the deformation.

The sensor device 2900 includes a set of conductive lines or traces 2908. Each trace 2908 is disposed on the substrate 2902 along a respective path between the cuts 2904. The traces 2908 electrically connect the strain gauges 2906 with bond or other contact pads 2910. In this example, each trace 2908 terminates at a respective one of the contact pads 2910 along the exterior of the substrate 2902. The contact pads 2910 may be used to connect the sensor device 2900 to another component, such as a controller, communication device, and/or power source.

FIG. 30 depicts a sensor device 3000 in accordance with one example. The sensor device 3000 may have a number of components and/or features in common with the devices described above. For instance, the sensor device 2900 includes a substrate 3002. In FIG. 30, the cuts in the substrate 3002 are not shown in the interest of ease in illustration of a number of conductive lines or traces 3004 disposed on the substrate 3002. The traces 3004 may be positioned between the cuts and otherwise configured as described herein.

The sensor device 3000 may include any type(s) of sensor structures. The sensor structures are also not shown for ease in illustration of the traces 3004. In some cases, a strain gauge or other strain sensor is disposed at interior ends of the traces 3004. In this example, each trace 3004 terminates at bond or other contact pads 3006, 3008. The contact pads 3006 may be used for connection(s) of the sensor device 3000 to one or more external (e.g., non-integrated) components as described above. Each contact pad 3008 may facilitate the electrical connection of a sensor structure via, for instance, soldering. Other types of connections may be used. For instance, the sensor structures may be integrated with the traces 3004 to any desired extent. In this example, the traces 3004 are configured to support four sensor structures. Any number of sensor structures may be included.

The disclosed devices may use circuit designs other than those shown in FIGS. 29 and 30. For instance, the paths along which the traces are disposed may vary with the cut patterns and/or the location, number, type, and/or other characteristics of the sensor structures.

The kirigami module described herein may be used to improve physical therapy, achieve desired athletic performance, or for other desired purposes. To these ends, real time (e.g., substantially real time) visualization and/or feedback on motion may be used. For instance, one example implementation of the kirigami module includes communication with a virtual reality headset and/or augmented reality platform (e.g. Apple AR Kit) to provide instruction and feedback to the user on how to perform certain motions for daily activities, physical therapy exercises, weight-lifting, stretching, yoga, etc. To aid with this implementation, a smartphone app may be used to provide real-time motion analysis to the user based on exercises, e.g., those prescribed by a physiotherapist. The smartphone app ascertains the orientation and extent of the imaged environment (e.g. a room), and an avatar is substantially superimposed on the captured image of the subject. The avatar then performs a motion, for instance, raising the arm along the elevation angle plane for the coordinate system used to describe the planes of motion. The user is instructed to perform the same motion, while the worn kirigami module tracks the position. Deviations from intended motion are highlighted on the screen (and/or trigger sounds, and/or haptic feedback), also providing the user with an assessment of progress over time in achieving desired range of motion.

The disclosed devices may include or otherwise be integrated with various types of sensors in addition to the above-described strain gauges. For instance, accelerometers, gyroscopes, magnetometers, sweat, electrocardiographic, humidity, UV, pressure, optical, acoustic, and radiation sensors, as well as antennas, may be included. Use of such sensors allows for the following functionalities: joint tracking/position monitoring, muscle tracking, heart rate monitoring, temperature readings, UV monitoring, neuromuscular electrical stimulations, brace support, breath monitoring, sleep monitoring, haptic feedback, lactic acid sampling, local anesthetic dosing, pulse oximetry, vocal vibration detection, and sound amplification. The disclosed devices may thus communicate a number of different types of data to the user, e.g., via mobile/portable devices, smart glasses, computer/laptops, watches, and virtual or augmented reality displays.

The above-described kirigami modules provide a customizable platform for the collection of data using a number and a variety of sensors suited to different applications. For example, in measuring the range of motion of a knee, or a shoulder, kirigami modules allow the placement of sophisticated but substantially rigid sensors dynamically in three dimensions when worn on the subject. As described above, the substantially rigid components may be placed between cut ends on the kirigami sheet, where there is minimal curvature upon deflection, while other sensing elements, such as strain gauges, which may involve significant deformation, may be placed at the maximum curvature, e.g., at the start of the cut.

The cut pattern may be determined based on the curvature of the body part. As described above, the disclosed devices may be applied to major joints such as shoulders, elbows, and knees, as well as to major muscles, such as the neck, triceps, and hip flexors. Still other cut patterns may be used for different regions of the foot, e.g., as part of a sock or sole of a shoe. Different cut patterns may be combined in one substrate, forming one continuous sheet to, e.g., conform to the topology of the foot The manner in which the disclosed devices are fabricated may vary. For instance, in other cases, the disclosed devices may be configured with wiring using a three-dimensional (3D) printed conductive filament, such as a carbon nanotube or graphene based filament. For example, a conductive filament may be 3D printed on a PET substrate, which is then laser cut to form a number of discontinuous concentric cuts. Alternatively or additionally, silver and/or another conductive material is deposited via vacuum thermal evaporation after cutting the PET substrate into the discontinuous, concentric cut pattern. Various other techniques for fabrication on e.g., a microscale, may be used, including microelectromechanical lithography techniques.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A sensor device comprising:
   a substrate having a plurality of cuts through the substrate to define a set of substrate sections, the substrate being flexible and, via the plurality of cuts, capable of conforming to a curved surface having a shape; and
   a plurality of sensor structures supported by the substrate, each sensor structure of the plurality of sensor structures being disposed at and on a respective substrate section of the set of substrate sections;
   wherein deformation of the substrate to conform the substrate to the curved surface deforms each respective substrate section of the set of substrate sections such that each respective substrate section is deformed to a respective extent, and
   wherein each sensor structure of the plurality of sensor structures is configured to provide an indication of the respective extent of the deformation and the shape of the curved surface.

2. The sensor device of claim 1, wherein the plurality of cuts are arranged such that the set of substrate sections are disposed in a concentric arrangement.

3. The sensor device of claim 2, wherein the concentric arrangement is symmetrical.

4. The sensor device of claim 1, wherein the plurality of cuts are arranged such that the set of substrate sections are disposed in multiple concentric arrangements, the multiple concentric arrangements being connected with one another.

5. The sensor device of claim 1, wherein the plurality of cuts are curvilinear.

6. The sensor device of claim 1, wherein the plurality of cuts are straight.

7. The sensor device of claim 1, wherein the substrate is capable of being disposed as a planar sheet.

8. The sensor device of claim 1, wherein:
   the plurality of sensor structures comprises a flexible sensor structure; and
   the set of substrate sections comprises a respective beam along which the flexible sensor structure is disposed.

9. The sensor device of claim 8, wherein the flexible sensor structure comprises a strain sensor.

10. The sensor device of claim 9, wherein the strain sensor comprises a strain gauge.

11. The sensor device of claim 1, further comprising a rigid sensor structure, the rigid sensor structure being disposed adjacent to, and between, ends of a pair of the plurality of cuts.

12. The sensor device of claim 11, wherein the rigid sensor structure comprises an inertial measurement unit.

13. The sensor device of claim 1, further comprising a circuit in which the plurality of sensor structures are disposed, the circuit comprising a lead supported by the substrate and routed between adjacent cuts of the plurality of cuts.

14. The sensor device of claim 13, wherein the circuit comprises a power source supported by the substrate and disposed adjacent to ends of a pair of the plurality of cuts.

15. The sensor device of claim 13, wherein the circuit comprises a microcontroller supported by the substrate and disposed adjacent to ends of a pair of the plurality of cuts.

16. The sensor device of claim 13, wherein the circuit comprises an impulse generator supported by the substrate and disposed adjacent to ends of a pair of the plurality of cuts.

17. The sensor device of claim 1, further comprising a flexible adhesive layer that extends across a lateral extent of the substrate, the flexible adhesive layer being configured to adhere the sensor device to a subject.

18. The sensor device of claim 17, wherein the plurality of sensor structures are disposed between the flexible adhesive layer and the substrate.

19. The sensor device of claim 18, further comprising a fabric layer worn by the subject, wherein the flexible adhesive layer is disposed between the fabric layer and the plurality of sensor structures.

20. The sensor device of claim 18, further comprising a fabric layer worn by the subject, wherein the fabric layer is disposed between the substrate and the subject.

21. The sensor device of claim 17, wherein the flexible adhesive layer is configured as a patch to be adhered to an article of clothing or to equipment configured to protect the subject.

22. A sensor system comprising:
a processor;
a memory in which tracking instructions and calibration data are stored; and
a sensor module comprising:
    a flexible substrate having a plurality of cuts through the substrate to define a kirigami structure, the flexible substrate being capable, via the plurality of cuts, of conforming to a curved surface having a shape; and
    a plurality of strain sensors supported by the flexible substrate, each strain sensor of the plurality of strain sensors being disposed on the kirigami structure at a respective location across the kirigami structure;
wherein execution of the tracking instructions by the processor causes the processor to generate data indicative of the shape of the curved surface and displacement of the sensor module based on the calibration data and output signals from the plurality of strain sensors.

23. The sensor system of claim 22, wherein the sensor module is a wearable module such that the displacement of the sensor module is representative of a three-dimensional curvature of a surface of the subject wearing the sensor module.

24. The sensor system of claim 22, further comprising a garment in which the sensor module is integrated.

25. The sensor system of claim 22, further comprising protective equipment configured to be worn by a user, wherein the sensor module is integrated into the protective equipment.

26. The sensor system of claim 25, wherein the protective equipment comprises a joint brace.

27. The sensor system of claim 22, wherein the sensor module comprises an adhesive layer configured to adhere the sensor module to a subject.

28. The sensor system of claim 22, wherein the displacement comprises an angular displacement.

29. The sensor system of claim 22, wherein the displacement comprises a translational displacement.

30. The sensor system of claim 22, wherein the execution of the tracking instructions causes the processor to determine a range of motion of a subject wearing the sensor module.

31. The sensor system of claim 22, wherein the execution of the tracking instructions causes the processor to determine an activity type in which a subject wearing the sensor module is engaged via pattern analysis of the data indicative of the displacement.

32. The sensor system of claim 22, further comprising an impulse generator supported by the flexible substrate and configured to provide an impulse to a subject wearing the sensor module in response to a direction from the processor, wherein the processor is configured to provide the direction based on an analysis of the data indicative of the displacement.

33. The sensor system of claim 22, further comprising a display in communication with the processor, wherein the processor is configured to display images on the display in accordance with graphics instructions stored in the memory, the images being representative of the data indicative of the displacement.

34. The sensor system of claim 22, further comprising a microcontroller supported by the flexible substrate, the microcontroller comprising the processor and the memory.

35. The sensor system of claim 22, wherein the memory comprises a volatile memory unit in communication with the processor, and further comprises a non-volatile storage device in which the calibration data is stored.

* * * * *